United States Patent [19]

LaMattina et al.

[11] Patent Number: 5,026,715

[45] Date of Patent: Jun. 25, 1991

[54] 2-GUANIDINO-4-ARYLTHIAZOLES FOR TREATMENT OF PEPTIC ULCERS

[75] Inventors: John L. LaMattina, Ledyard; Peter A. McCarthy, Pawcatuck; Lawrence A. Reiter, Mystic, all of Conn.

[73] Assignee: Pfizer Inc., New York, N.Y.

[21] Appl. No.: 426,455

[22] Filed: Oct. 20, 1989

Related U.S. Application Data

[63] Continuation of Ser. No. 178,058, filed as PCT US86/01795 on Aug. 29, 1986, abandoned.

[51] Int. Cl.$^5$ .................. C07D 417/04; A61K 31/425
[52] U.S. Cl. .................................... 514/326; 514/370; 546/209; 548/181
[58] Field of Search ................ 548/198, 181; 514/326, 514/370; 546/209

[56] References Cited

U.S. PATENT DOCUMENTS

| | | | |
|---|---|---|---|
| 3,591,584 | 7/1971 | Lombardino | 260/243 |
| 3,758,491 | 9/1973 | Capps | 260/306.7 |
| 4,293,549 | 10/1981 | Rachlin et al. | 424/245 |
| 4,374,843 | 2/1983 | LaMattina et al. | 424/270 |
| 4,435,396 | 3/1984 | LaMattina et al. | 424/248.51 |
| 4,560,690 | 12/1985 | Reiter | 514/256 |
| 4,791,200 | 12/1988 | Press | 544/369 |

FOREIGN PATENT DOCUMENTS 59-225172 12/1984 Japan .
59-225186 12/1984 Japan .

OTHER PUBLICATIONS

*Medicinal Chemistry*, Third Edition, Alfred Burger, Ed., Wiley-Interscience, pp. 75–77.
Rachlin, S. et al., "Basic Antiinflammatory Compounds, N,N',N''-Trisubstituted Guanidines", J. Med. Chem. 23, 13–20 (1980).
Lombardino, J. et al., "Potent Antiinflammatory N-Heterocyclic 3-Carboxamides of 4-Hydroxy-2-Methyl-2H-1,2-Benzothiazine 1,1-Dioxide", *J. Med. Chem.* 16, 493–496 (1973).

*Primary Examiner*—Robert Gerstl
*Attorney, Agent, or Firm*—Peter C. Richardson; J. Trevor Lumb; Gregg C. Benson

[57] ABSTRACT

2-Guanidino-4-arylthiazole compounds of the formula

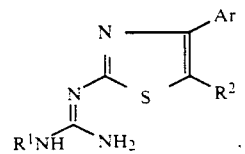

a pharmaceutically acceptable cationic or acid addition salt thereof wherein
$R^1$ is hydrogen, ($C_1$-$C_{10}$)alkyl, optionally substituted phenyl or certain optionally substituted aralkyl groups;
$R^2$ is hydrogen or ($C_1$-$C_4$)alkyl, and
Ar is certain optionally substituted pyrrolyl or indolyl groups; method for their use in treatment of gastric ulcers, by inhibition of parietal cell $H^+/K^+$ ATPase, and antiinflammatory conditions in combination with piroxicam, for use in mammals, and pharmaceutical compositions containing said compounds.

25 Claims, No Drawings

2-GUANIDINO-4-ARYLTHIAZOLES FOR TREATMENT OF PEPTIC ULCERS

This is a continuation of application Ser. No. 178,058, filed as PCT US86/01795 on Aug. 29, 1986, now abandoned.

TECHNICAL FIELD

The present invention relates to novel 2-guanidino-4-arylthiazole compounds wherein said 4-aryl group is a pyrrolyl or indolyl, each aryl group being optionally substituted, which are cytoprotectants and inhibitors of the $H^+/K^+$ ATPase enzyme, method for their use in treating peptic ulcers in mammals, including humans; compositions containing said compounds; and method for treatment of inflammation in said mammals by administering said compounds in combination with piroxicam and compositions containing said combination with piroxicam.

BACKGROUND ART

Chronic gastric and duodenal ulcers, together known as peptic ulcers, are a common ailment for which a variety of treatments, including dietary measures, drug therapy and surgery, may be employed, depending on the severity of the condition. Particularly valuable therapeutic agents useful for the treatment of gastric hyperacidity and peptic ulcers are the histamine-$H_2$ receptor antagonists, which act to block the action of the physiologically active compound histamine at the $H_2$-receptor sites in the animal body and to thereby inhibit the secretion of gastric acid.

U.S. Pat. No. 4,374,843 issued Feb. 22, 1983, U.S. Pat. No. 4,435,396 issued Mar. 6, 1984 and U.S. Pat. No. 4,560,690 issued Dec. 24, 1985 disclose 2-guanidino-4-imidazolylthiazoles, 2-guanidino-4-(1,2,4-triazolyl)-thiazoles and 2-guanidino-4-thiazolylthiazoles which are useful for treatment of gastric hyperacidity and peptic ulcers, some of which are also cytoprotective agents. Piroxicam, 4-hydroxy-2-methyl-N-2-pyridinyl-2H-1,2-benzothiazine-3-carboxamide 1,1-dioxide, is a known anti-inflammatory agent, see, e.g., U.S. Pat. No. 3,591,584; and J. Lombardino et al., *J. Med. Chem.*, 16, 493 (1973).

DISCLOSURE OF THE INVENTION

The present invention relates to a novel class of compounds which are useful in treating gastric ulcers in mammals by virtue of their activity as inhibitors of the gastric parietal cell, $H^+/K^+$ ATPase, the enzyme ultimately responsible for hydrogen ion secretion. Said compounds are of the formula

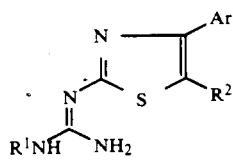
(I)

a pharmaceutically acceptable cationic or acid addition salt thereof, wherein $R^1$ is H, a straight chain or branched chain $(C_1-C_{10})$alkyl, $(R^4)_pC_6H_3$ or $(R^4)_pAr^1(CH_2)_n$ where p is zero, 1 or 2; n is an integer from 1 to 4, the $R^4$ groups are the same or different and are H, F, Cl, Br, I, $CH_3$, $CH_3O$, $NO_2$, OH, CN, $COOR^5$ or $OCOR^5$ and $R^5$ is $(C_1-C_3)$alkyl;

$Ar^1$ is the residue of a phenyl, naphthyl, furyl, thienyl, pyridyl, pyrimidinyl, thiazolyl or imidazolyl group, $R^2$ is H or $(C_1-C_4)$alkyl; and Ar is

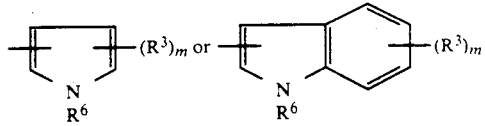

where m is 1, 2 or 3;

$R^6$ is H, $(C_1-C_4)$alkyl or $R^{10}SO_2$ and $R^{10}$ is $(C_1-C_4)$alkyl, phenyl, tolyl, benzyl or phenylethyl; and $R^3$ is a substituent attached to any carbon atom in the Ar group other than one at a ring junction, at least one $R^3$ is H or $(C_1-C_4)$alkyl and each of the remaining $R^3$ is H, $(C_1-C_4)$alkyl, $(C_1-C_4)$alkoxy, $(R^4)_2C_6H_3$, $(R^4)_2C_6H_3(CH_2)_n$, $(R^4)_2C_6H_3(CH_2)_nO$, $COOR^7$, $COR^8$, $NHCOR^8$, $NHCH_2R^8$, $NR^8R^9$, $(CH_2)_nNR^8R^9$, $(CH_2)_{n-1}CONR^8R^9$, OH, CN, $CF_3$, F, Cl or Br, wherein n and $R^4$ are as previously defined;

$R^7$ is H, $(C_1-C_4)$alkyl or benzyl;

$R^8$ and $R^9$ taken separately are each H, $(C_1-C_{10})$alkyl, phenyl or benzyl, or when taken together with the nitrogen atom to which they are attached, form a 5-membered or 6-membered ring, optionally containing an atom of O or S or the group $NR^{11}$ as a ring member and $R^{11}$ is H, methyl or ethyl;

with the proviso that when Ar is

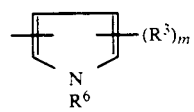

and each $R^3$ is H, at least one of $R^1$, $R^2$ or $R^6$ is other than H;

In each case, above, the bracketed range of carbon atoms refers to the total number of carbon atoms in the group. The carbon chain can be straight or branched.

Pharmaceutically acceptable acid addition salts are those with from one to three equivalents of the acid, and especially with one or two equivalents. Suitable acids include, but are not limited to, HCl, HBr, $H_2SO_4$, $H_3PO_4$, $CH_3SO_3H$, p-toluenesulfonic acid, maleic acid, fumaric acid, succinic acid and citric acid. For a current list of such salts see, e.g., Berge et al., *J. Pharm. Sci.*, 66, 1-19 (1977).

Because of their facile preparation and high level of antisecretory activity, $H^+/K^+$ ATPase inhibitory activity and/or cytoprotective activity as evidenced in tests for inhibition of ethanol-induced ulcers, preferred compounds of formula (I) are:

(1) of the formula

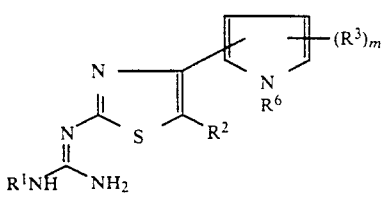

(II)

wherein $R^1$, $R^2$, $R^3$ and $R^6$ are as defined above; particularly preferred such compounds are those wherein $R^1$ is H, $(R^4)_2C_6H_3CH_2$, $(C_4-C_8)$alkyl, furylmethyl or thienylmethyl; $R^2$ is H or methyl, one $R^3$ is a substituent bonded to the 2-position of the pyrrole group and another $R^3$ is H, $(C_1-C_4)$alkyl, $COOR^7$, CHO, $(CH_2)_nNR^8R^9$ or $CONR^8R^9$;

(2) of the formula

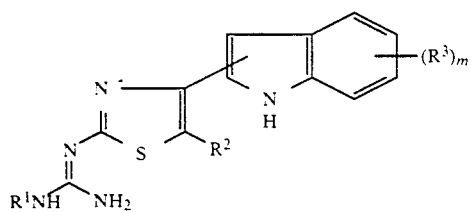

(III)

and particularly such compounds wherein $R^1$ is H, $(R^4)_2C_6H_3CH_2$, $(C_4-C_8)$alkyl, furylmethyl or thienylmethyl; $R^2$ is H or $CH_3$, $R^3$ is H, F, Cl, Br, OH, $(C_1-C_4)$alkoxy, $(C_1-C_4)$alkyl, $R^4C_6H_4$, $NHCOR^8$, $(CH_2)_nNR^8R^9$, $R^4C_6H_4CH_2O$, CN or $COOR^7$; and the thiazole group is bonded to the 2, 3 or 5-position of the indole;

Especially preferred pyrrolyl thiazoles (II) of the invention are of the formula

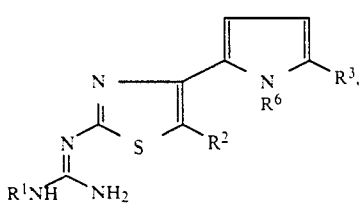

(IV)

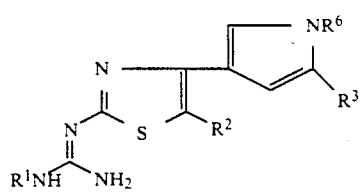

(V)

or

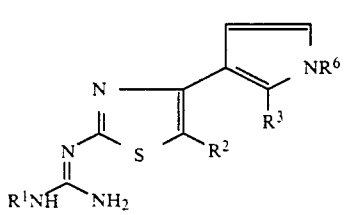

(VII)

wherein $R^1$, $R^2$, $R^3$ and $R^6$ are as previously defined.

Most especially preferred invention compounds are the indolylthiazoles of the formulae

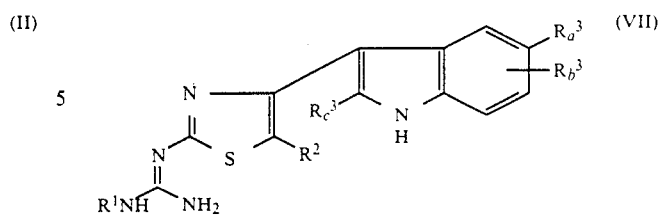

(VII)

where $R_a^3$ and $R_b^3$ are as defined above for $R^3$ and $R_c^3$ is H or $(C_1-C_4)$alkyl; and

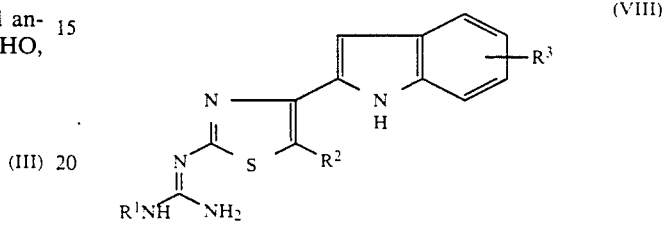

(VIII)

wherein $R^1$, $R^2$ and $R^3$ are as previously defined.

The most particularly preferred specific compounds of the invention are 2-guanidino-4-[(2-piperidinocarbonyl)pyrrol-4-yl]thiazole,
2-guanidino-4-(2-methylpyrrol-4-yl)thiazole,
2-guanidino-4-(5-methylpyrrol-2-yl)thiazole,
2-guanidino-4-[(2-methyl-1-phenylsulfonyl)pyrrol-4-yl]thiazole,
2-guanidino-4-[(5-methyl-1-phenylsulfonyl)pyrrol-2-yl]thiazole,
2-(N-benzylguanidino)-4-(2-methylpyrrol-4-yl)thiazole,
2-(N-benzylguanidino)-4-(pyrrol-2-yl)thiazole,
2-(N-benzylguanidino)-4-(2-methylpyrrol-3-yl)thiazole,
2-(N-benzylguanidino)-4-(1-phenylsulfonyl-2-methyl)-pyrrol-3-yl]-5-methylthiazole,
4-(1H-indol-3-yl)-2-(N-benzylguanidino)thiazole,
4-(5-methoxy-1H-indol-3-yl)-2-(N-benzylguanidino)-thiazole,
4-(5-chloro-1H-indol-3-yl)-2-(N-benzylguanidino)-thiazole,
4-(1H-indol-3-yl)-2-guanidinothiazole,
4-(5-methoxy-1H-indol-3-yl)-2-guanidinothiazole,
4-(5-chloro-1H-indol-3-yl)-2-guanidinothiazole,
4-(2-methyl-1H-indol-3-yl)-5-methyl-2-guanidino-thiazole,
4-(2-methyl-1H-indol-3-yl)-5-methyl-2-(N-benzyl-guanidino)thiazole,
4-(1H-indol-2-yl)-2-guanidinothiazole, and
4-(1H-indol-2-yl)-2-(N-benzylguanidino)thiazole.

The present invention further relates to a pharmaceutical composition useful for treating gastric ulcers in a mammal, including a human, by inhibiting gastric parietal cell $H^+/K^+$ ATPase which comprises a pharmaceutically acceptable diluent or carrier and a gastric parietal cell $H^+/K^+$ ATPase inhibiting amount of a compound of formula (I). Additionally, the invention relates to a method of treating gastric ulcers in a mammalian subject in need of such treatment by inhibiting parietal cell $H^+/K^+$ ATPase which comprises administering to the subject a parietal cell $H^+/K^+$ ATPase inhibiting amount of a compound of formula (I).

Further, the invention provides an antiinflammatory composition comprising an antiinflammatory effective amount of piroxicam or a pharmaceutically acceptable salt thereof and a gastric parietal cell $H^+/K^+$ inhibiting amount of a compound of the formula (I); and a method of treating inflammation in a mammal comprising administration to said mammal of an antiinflammatory effective amount of piroxicam or a pharmaceutically acceptable salt thereof and a gastric parietal cell $H^+/K^+$ ATPase effective amount of a compound of the formula (I).

DETAILED DESCRIPTION OF THE INVENTION

The 4-aryl-2-guanidinothiazoles of formula (I) are prepared, for example, by the following reaction scheme:

Scheme 1

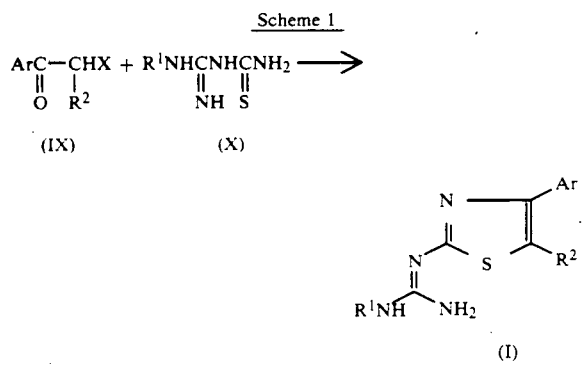

Approximately equimolar amounts of the guanylthiourea of formula (X) and aryl-$R^2$-substituted-alpha-haloketone of formula (IX), wherein $R^1$, $R^2$ and Ar are as previously defined and X is chloro or bromo, are reacted in the presence of a reaction-inert solvent such as tetrahydrofuran, a lower alkanol such as methanol, ethanol or isopropanol; a lower alkyl ketone such as acetone or methylethylketone; dimethylsulfoxide or N,N-dimethylformamide. Preferred solvents are acetone and N,N-dimethylformamide. A preferred temperature for the above reaction to provide compounds of formula (I) is from about 20° to 120° C. and especially from about 25° to 60° C. Under these conditions the formation of the desired product of formula (I) is substantially complete in from about 30 minutes to 24 hours, after which the product (I) is isolated by standard methods, well known in the art. For example, by cooling the reaction mixture to form a precipitate, evaporation of solvent or by addition of a nonsolvent, such as ethyl ether, to obtain the product in the form of its hydrochloride or hydrobromide salt. The salt is readily converted to the free base of formula (I) by standard neutralization/extraction methods. To obtain other pharmaceutically acceptable acid addition salts, the free base is taken up in an organic solvent and either one, two or three equivalents of acid corresponding to the desired salt is added. The salt is then recovered by filtration, concentration or addition of a nonsolvent, or by a combination of these methods.

Preferred values of Ar for the invention compounds of formula (I) give rise to compounds of formula (II) and (III) as defined above.

Compounds of formulae (II) or (III) where $R^3$ is $CH_2NH_2$, $(CH_2)_nNR^8R^9$ or $NHCH_2R^8$ are prepared, for example, by reduction of the corresponding compounds wherein $R^3$ is CN or an amide of formula $(CH_2)_{n-1}CONR^8R^9$ or $NHCOR^8$, respectively. Preferred reducing agents for the above reactions are the commercially available metal hydrides known in the art to be useful for such reductions. Examples of such metal hydrides are lithium aluminum hydride, lithium triethylborane, borane or diborane. Preferred reducing agents are borane/tetrahydrofuran, diborane/tetrahydrofuran and lithium aluminum hydride. Typically, the reduction is carried out under substantially anhydrous conditions and in the presence of a suitable reaction inert solvent, e.g., ethyl ether, tetrahydrofuran, 1,2-dimethoxyethane or diethyleneglycol dimethylether. A preferred range of temperature for these reduction reactions is from $-70°$ to 80° C. and especially from room temperature to 60° C. Under these conditions the reduction is completed in from about 2 to 24 hours, after which the excess reducing agent is quenched, e.g., by cautious addition of wet solvent or ethyl acetate and the product isolated by standard extraction/evaporation methods and purified, if desired, by recrystallization or by column chromatography.

In like manner aldehydes of formula (II) or (III) where $R^3$ is CHO are reduced, preferably with sodium borohydride, to obtain the corresponding compounds wherein $R^3$ is methyl. Typically such a reduction is carried out in a lower alkanol solvent such as methanol, ethanol or isopropanol at a temperature of from room temperature up to the reflux temperature of the solvent.

Hydrolysis of a compound (II) or (III) wherein $R^6$ is $R^{10}SO_2$ as defined above affords the corresponding compound where $R^6$ is H. Typically the reaction is carried out in the presence of a strong base such as sodium hydroxide, sodium carbonate or potassium hydroxide, in aqueous solvent, preferably aqueous methanol or ethanol. While the hydrolysis can be carried out over a broad range of temperatures, a preferred temperature is from about room temperature up to 85° C., and the reflux temperature of the solvent is especially preferred for reasons of efficiency and convenience.

The starting alpha-halomethylaryl ketones (IX) are prepared, for example, by acylation of the appropriate ArH compound with an alpha-haloacid halide by the well-known Friedel-Crafts reaction.

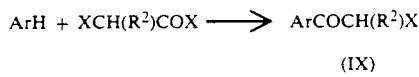

(IX)

where Ar, R and X are as previously defined. For a review of the Friedel-Crafts reaction see e.g., Groves, *Chem. Soc. Rev.* 1, 73 (1972).

Alternatively, the starting ketones (IX) are obtained by Friedel-Crafts acylation with an acid anhydride followed by halogenation as shown below.

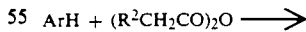

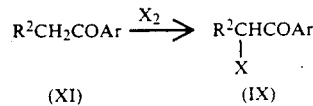

For starting compounds (IX) where Ar is one of the above pyrrole derivatives, the reaction is typically carried out with anhydrous aluminum chloride or boron trifluoride etherate as catalyst in a halogenated hydrocarbon solvent, preferably 1,2-dichloroethane or chloroform, at or about room temperature. For preparation of the indole derivatives of formula (XI), however, the acylation is typically carried out in the presence of pyridine and toluene at somewhat elevated temperature, preferably 40°-80° C. The halogenation of intermediate ketones (XI) is ordinarily carried out by controlled addition of an equimolar amount of elemental bromine or chlorine to a solution of the intermediate (XI) in a halogenated hydrocarbon solvent such as chloroform or methylene dichloride at a temperature of from about −20° to +25° C. The resulting mixture is then stirred at the temperature of the addition and/or at room temperature for several hours to complete the reaction.

A useful method for preparation of compounds (IX) where Ar is indolyl is by acylation of the appropriate indolyl Grignard reagent. For example, reaction of a 5-substituted, or 2,5-disubstituted indole with methylmagnesium chloride in ethyl ether under anhydrous conditions in the cold affords a 1,3-bis-methylmagnesium indole intermediate in situ. This is immediately acylated with an acid halide of the formula $R^2CH(X^1)COX^2$ where $X^1$ is H, Cl or Br and $X^2$ is Cl or Br, to provide the corresponding 1,3-diacylated indole. The latter is then selectively hydrolyzed to remove the 1-acyl group, e.g., with methanolic potassium carbonate at ambient temperature, to provide the desired 3-alkanoyl- or 3-(α-haloalkanoyl)indole of formula (IX).

Other methods for obtaining the starting alphahaloketones of formula (IX) are outlined below.

1. 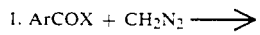

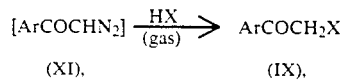

2. 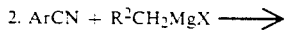

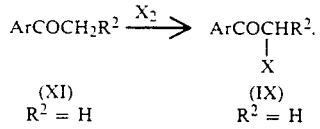

In the first reaction sequence the aryl carbonyl chloride, obtained by reaction of the corresponding carboxylic acid with thionyl chloride, phosgene or acetyl chloride/phosphorus pentachloride by well-known methods, is reacted with diazomethane in reaction inert solvent, such as ethyl ether, to form the diazo ketone. The diazo ketone is then reacted with gaseous hydrogen halide to form the desired starting compound (IX) where $R^2$ is H. In the second such method the corresponding arylnitrile (ArCN) is reacted with an equimolar amount of Grignard reagent, $R^2CH_2MgX$, where X is Cl or Br, followed by contacting the resulting iminomagnesium halide complex with water to generate the ketone, $ArCOCH_2R^2$, which is then halogenated as described above to form the starting compound (IX).

The requisite starting guanylthioureas of formula (X) wherein $R^1$ is as previously defined, are prepared, for example, by reaction sequence outlined below.

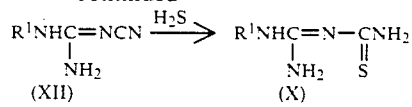

In the first step above the N-cyanoguanidine compounds (XII) are prepared by reaction of the appropriate amine ($R^1NH_2$) and dicyanimide in approximately equimolar amounts by methods previously described by Curd et al., *J. Chem. Soc.*, 1630 (1948) and by Redmon and Nagy in U.S. Pat. No. 2,455,807. Typically, the reactants are heated in the presence of a polar organic solvent, e.g., a ($C_1$-$C_4$)alkanol, water or mixtures thereof, preferably n-butanol, at a temperature of from 40° to 120° C., preferably at the reflux temperature of the solvent. The N-cyanoguanidine product is then isolated, e.g., by cooling, filtering to remove precipitated salts and evaporation of the filtrate.

The guanylthiourea intermediates (X) are obtained by reaction of the appropriate N-cyanoguanidine (XII) with hydrogen sulfide. This reaction is ordinarily carried out in the presence of a polar organic solvent such as a ($C_1$-$C_4$)alkanol, acetone, ethyl acetate or dimethylsulfoxide; a preferred solvent is methanol. Typically, the reaction is carried out in the presence of a catalytic amount of a secondary amine, preferably diethylamine. The reaction can be carried out at atmospheric pressure or a higher pressure, e.g., at 3 to 10 atmospheres, and at a temperature of from about 10° to 100° C., preferably from 25° to 80° C. Of course, when the reaction is run at a higher temperature within the preferred range, the reaction time will be shorter. Conversely, at a lower temperature the reaction time required will be longer. The product is ordinarily isolated simply by evaporation of solvent. In many cases the crude product, thusly obtained, is of sufficient purity for use in the next reaction step. Alternatively, the crude product can be purified, e.g., by column chromatography.

The details of the methods for providing the starting guanylthioureas (X) and the amines, $R^1NH_2$, used in their preparation are set forth in the embodiment below, and in U.S. Pat. No. 4,560,690.

The pharmaceutically acceptable acid addition salts of the novel compounds of formula (I) are also embraced by the present invention. The salts are readily prepared by contacting the free base with an appropriate mineral or organic acid in either aqueous solution or in a suitable organic solvent. The solid salt may then be obtained by precipitation or by evaporation of the solvent. Especially preferred salts are the hydrochloride and dihydrochloride.

The utility of the present compounds as antiulcer agents is reflected in vitro by their inhibition of $H^+/K^+$ ATPase isolated from canine gastric mucosa. The enzyme activity was assayed according to Beil et al., *Brit. J. Pharmacol.* 82, 651–657 (1984) with slight modifications. The enzyme (1-2 micrograms) was preincubated at 37° C. for 45 minutes with a medium containing $2 \times 10^{-3}M$ $MgCl_2$, 0.05M Tris-Cl buffer (pH 7.5) with or without 0.01M KCl, and the acid activated test drug in a final volume of 0.590 ml. The reaction was started by the addition of 0.010 mmol of ATP (final concentration $3 \times 10^{-3}M$). The reaction was terminated by adding trichloroacetic acid to a concentration of 4.2%. Liberated inorganic phosphate was determined using Fiske and Subbarow Reducer available commercially (e.g., from Sigma Chemical Co., P.O. Box 14508, St. Louis, Mo. 63178, U.S.A.). In this test the drugs are preferably first acid activated by incubating in 1:1 dimethylsulfoxide:0.02N HCl at 37° C. for 30 minutes. In this test the preferred compound 4-(1H-indol-3-yl)-2-(N-benzylguanidino)thiazole hydrochloride showed an IC$_{50}$ (i.e., the concentration which inhibits the enzyme to the extent of 50%) of $2\times10^{-6}$M; 4-(5-chloro-1H-indol-3-yl)-2-(N-benzylguanidino)thiazole had an IC$_{50}$ of $0.6\times10^{-6}$M; 2-guanidino-4-(2-methylpyrrol-4-yl)thiazole had an IC$_{50}$ of $15\times10^{-6}$M and 4-(3-methoxyphenyl)-2-(N-benzylguanidino)thiazole had an IC$_{50}$ of $10\times10^{-6}$M.

The in vivo utility of the present compounds as antiulcer agents is also particularly shown by their cytoprotective activity. Such activity is demonstrated by the inhibition of ethanol-induced gastric ulceration in rats, using the method of Example 18 of U.S. Pat. No. 4,560,690. In this test, preferred 2-guanidino-4-(2-methylpyrrol-4-yl)thiazole at a dose of 30 mg/kg gave 100% inhibition and 2-(N-benzylguanidino)-4-(pyrrol-2-yl)thiazole gave 99% inhibition.

The in vivo utility of the present compounds as antiulcer agents is, in part, reflected by their gastric antisecretory activity in rats by the following method:

A rat is placed in an ether jar until it has no blink reflex or pinch reflex (usually the rat is slightly cyanotic). The rat is then placed on its back, an ether cone is placed over its nose. It is important to monitor the coloring of the rat, and to remove the cone if the rat becomes excessively blue. With rat tooth forceps, the skin is lifted and an incision is made with small scissors from 2 cm below the sternum to the sternum. The muscle layer is cut in the same manner, exposing a view of the liver. The large lobe of the liver is gently lifted with straight smooth forceps exposing the pancreatic tissue and the intestine. The intestine is gently elevated and the pylorus sphincter is localized without touching the stomach. Curved forceps are carefully inserted beneath the pylorus. A length of silk thread (approximately 10 cm) is pulled through and snugly tied in a square knot. If the blood vessel is severed during the process, the rat is not used since the blood supply to the stomach will have been severely compromised under such conditions. An injection of drug or vehicle is made into the duodenum. The rat is lifted up by grasping above and below the incision, and the abdominal contents are gently inserted back into the cavity. The incision is closed with wound clips. Subsequent to stapling of wounds, rats are housed in show box cages with other surgerized rats, 4/cage. Within 15 minutes rats appear to be fully recovered from the ether anesthesia. They are carefully monitored for bleeding, which can occur if the staples are not properly positioned. Two hours after surgery the rat is sacrificed by i.p. injection of sodium pentabarbitol (1 ml/kg). Rat tooth forceps are used to lift the abdomen, and it is then cut open with dissecting scissors. The large lobe of the liver is lifted. The esophagus is located under the smaller lobe of the liver. Curved forceps are placed under the esophagus and it is lifted. A hemostat is used to clamp off the esophagus from the stomach and to gently cut the stomach free. In a funnel over a borosilicate tube, the stomach is cut along the greater curvature releasing the contents. The last of the contents is squeezed out. The fluid containing tubes are spun in the centrifuge at 3000× rpm for 15 minutes at room temperature. The supernatants are carefully removed with pasteur pipettes, and placed in the graduated centrifuge tubes. Volumes are recorded. An automatic titrator (endpoint=pH 7.0) is used to determine pH and microequivalents of acid output/hr/100 g rat body weight. Results are reported as % inhibition of acid secretion in mg/kg.

The oral protective effect of the present compounds on piroxicam-induced gastric lesions is determined in rats according to the method of Example 1 of U.S. Pat. No. 4,559,326.

For the treatment (prophylactic and therapeutic) of gastric ulcers in a mammalian subject by inhibiting gastric parietal cell $H^+/K^+$ ATPase, the products of the present invention are administered by a variety of conventional routes of administration including oral and parenteral. Preferably, the compounds are administered orally. In general, these compounds will be administered orally at doses between about 0.25 and 50 mg/kg body weight of the mammalian subject to be treated per day, preferably from about 0.5 to 30 mg/kg per day, in single or divided doses. If parenteral administration is desired, then these compounds can be given at total daily doses between about 0.2 and 20 mg/kg body weight of the mammalian subject to be treated. In a 100 Kg man, this translates to a daily oral dosage of about 25-5000 mg/day (preferably about 50-3000 mg/day) and a parenteral dosage of about 20-2000 mg/day. However, at the discretion of the attending physician, some variation in dosage will necessarily occur, depending upon the condition of the subject being treated and the particular compound employed.

When co-administering piroxicam and a compound of the formula (I) to a mammal, particularly man, the oral route is preferred. The piroxicam is generally dosed in the range of about 0.1 to 1 mg/kg/day (or about 10-100 mg/day in a 100 Kg man), in single or multiple doses. The compound of the formula (I) is dosed according to the dosage regimen noted above. If desired, the compounds are dosed separately, but they are preferably co-administered in a single, combined formulation suitable for single or multiple daily dosage, as desired. Again, at the discretion of the attending physician, there can be some variation in this dosage regimen.

The compounds of the formula (I) are administered alone or in combination with piroxicam. In either case, the active ingredients will generally be further combined with pharmaceutically acceptable carriers or diluents. Suitable pharmaceutical carriers include inert diluents or fillers, sterile aqueous solutions and various organic solvents. The pharmaceutical compositions formed by combining the novel compounds of formula (I) or salts thereof and pharmaceutically acceptable carriers are readily administered in a variety of dosage forms such as tablets, powders, capsules, lozenges, syrups and the like. These pharmaceutical compositions can, if desired, contain additional ingredients such as flavorings, binders, excipients and the like. Thus, for oral administration, tablets containing various excipients, such as sodium citrate, are employed together with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tableting purposes. Solid compositions of a similar type may also be employed as fillers in soft and hard filled gelatin capsules. Preferred materials therefor include lactose or milk sugar and high molecular weight polyethylene glycols. When aqueous suspensions or elixirs are desired for oral administration, the essential active ingredient therein may be combined with various sweetening or flavoring agents, coloring matters or dyes and, if desired, emulsifying agents or suspending agents, together with diluents such as water, ethanol, propylene glycol, glycerin, or combinations thereof.

Preferably, the products of this invention are administered orally in unit dosage form, i.e., as a single physically discrete dosage unit containing an appropriate amount of the active compound in combination with a pharmaceutically acceptable carrier or diluent. Examples of such unit dosage forms are tablets or capsules containing from about 5 to 1,000 mg of the active ingredient, the compound of formula (I) comprising from about 10% to 90% of the total weight of the dosage unit.

For parenteral administration, solutions or suspensions of the compounds of formula (I) in sterile aqueous solutions, for example aqueous propylene glycol, sodium chloride, dextrose or sodium bicarbonate solutions are employed. Such dosage forms are suitably buffered if desired. The preparation of suitable sterile liquid media for parenteral administration will be well known to those skilled in the art.

The present invention is illustrated by the following examples. However, it should be understood that the invention is not limited to the specific details of these examples. All temperatures are in degrees centigrade. Nuclear magnetic resonance spectra (NMR) were measured for solutions in deuterated chloroform (CDCl$_3$) deuterated methanol (CD$_3$OD) or deuterated dimethyl sulfoxide (DMSO-d$_6$), and peak positions are reported in parts per million downfield from tetramethylsilane. The following abbreviations for peak shapes are used: bs, broad singlet; s, singlet; d, doublet; t, triplet; q, quartet; m, multiplet.

EXAMPLE 1

A. 1-(2-Formylpyrrol-4-yl)-2-chloroethanone

A mixture of 35 g (0.37 mole) pyrrole-2-carboxaldehyde in 325 ml dichloroethane was stirred under nitrogen in a three-necked, one-liter, round-bottomed flask fitted with an overhead stirrer and addition funnel. To this was added, in portions over a one-hour period, 294 g (2.21 mole) aluminum chloride. After the addition was completed, the mixture was stirred at room temperature for 10 minutes, then 124.7 g (88 ml, 1.10 mole) of chloroacetyl chloride was added dropwise over a one-hour period. The mixture was stirred at room temperature for 16 hours, then carefully poured into one liter of ice-water. The resulting precipitate (purple) was collected, washed well with water, and dried in vacuo. The dry solid was placed in a Soxhlet extractor and extracted with ethyl acetate for 20 hours. Concentration of the ethyl acetate solution afforded 59.4 g (94%) of the title compound as a yellow-green solid; m.p. 178°–179° C. This intermediate was used immediately in the next step. An analytical sample could be prepared by recrystallization from acetone.

Analysis calculated for C$_7$H$_6$ClNO$_2$: C, 49.00; H, 3.52; N, 8.16%. Found: C, 48.84; H, 3.53; N, 8.03%.

B. Employing the appropriate formylpyrrole as starting material in the above procedure afforded the following compound of formula (IX) in like manner.

| Compound (IX) | % Yield | M.P., °C. | Comment |
|---|---|---|---|
| 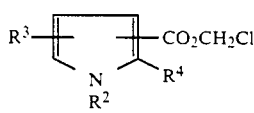 | 67 | 178–179 | Anal. Calc'd for C$_7$H$_6$ClNO$_2$: C, 49.00; H, 3.52; N, 8.16%. Found: C, 48.84; H, 3.53; N, N, 8.03%. |

EXAMPLE 2

A.
1-(2-N,N-dimethylaminocarbonylpyrrol-4-yl)-2-chloroethanone

Aluminum chloride (146.4 g, 1.1 mole) was slurried in 275 ml of dry 1,2-dichloroethane under nitrogen in a one-liter, three-necked, round-bottomed flask at room temperature. To this was added dropwise 43.7 ml (62 g, 0.55 mole) of chloroacetylchloride over 20 minutes. The mixture was stirred at room temperature for 50 minutes, a solution of 25.3 g (0.18 mole) of 2-N,N-dimethylcarboxamidepyrrole in 175 ml of 1,2-dichloroethane was added dropwise over 45 minutes. After the addition was completed, the mixture was stirred at room temperature for 18.5 hours and cautiously poured into one liter of ice-water. The resulting precipitate was collected, washed well with water, then with 1,2-dichloromethane and dried in vacuo. Recrystallization from ethanol afforded 24.2 g (62%) of the product as a crystalline solid; m.p. 193°–195.5° C.

(IX)

$$R^3 \underset{\underset{R^2}{N}}{\overline{\phantom{XXX}}} CO_2CH_2Cl \atop R^4$$

| Compound (IX) | % Yield | M.P. °C. | Comment |
|---|---|---|---|
| ClCH$_2$C(=O)—[pyrrole, NH, CH$_3$]—CON(CH$_3$)$_2$ | 44 | 146–149 | Purified by silica gel column chromatography, 10:1 CH$_2$Cl$_2$/CH$_3$OH as eluent. |

-continued

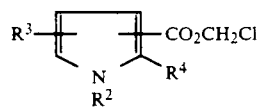
(IX)

| Compound (IX) | % Yield | M.P. °C | Comment |
|---|---|---|---|
| ClCH₂C(O)-pyrrole-C(O)N(piperidine), NH | 50 | 150 | Anal. Calc'd for $C_{12}H_{15}ClN_2O_2$: C, 56.58; H, 5.94; N, 11.00%. Found: C, 56.18; H, 5.80; N, 10.67%. |
| ClCH₂C(O)-pyrrole(N-CH₃)-CH₃ | 34 | 120–122 | |
| ClCH₂C(O)-pyrrole-NH | 11 | 118 | Recrystallized from 3:1 petroleum ether/ethyl acetate. |

EXAMPLE 3

1-(2-Methyl-1-phenylsulfonylpyrrol-3-yl)ethanone and 1-(2-methyl-1-phenylsulfonylpyrrol-4-yl)ethanone from 2-methyl-1-phenylsulfonylpyrrole A. A suspension of 89.3 g (0.66 mole) of aluminum chloride in one liter 1,2-dichloroethane was stirred at room temperature under nitrogen and 33.7 g (31.1 ml, 0.33 mole) acetic anhydride was added dropwise over 20 minutes. After the addition was completed, a solution of 24.3 g (0.11 mole) of 2-methyl-1-phenylsulfonylpyrrole in 155 ml of 1,2-dichloroethane was added dropwise over 15 minutes. The mixture was stirred at room temperature for two hours, then cautiously poured into one liter of ice-water. The biphasic mixture was extracted with methylene chloride (3×400 ml), the combined extracts dried (Na₂SO₄), filtered, and solvent evaporated to afford an oil which was a mixture of the two isomeric products. The mixture was separated by silica gel chromatography using 19:1 toluene/ethyl acetate as eluent. The less polar material proved to be 1-(2-methyl-1-phenylsulfonylpyrrol-3-yl)ethanone; m.p. 64°–67° C.; 17.3 g (60%).

¹H-NMR(CDCl₃)ppm(delta): 2.36 (s, 3H), 2.63 (s, 3H), 6.58 (d, 1H), 7.33 (d, 1H), 7.5–8.1 (m, 5H).

Analysis calculated for $C_{13}H_{13}NO_3S$: C, 59.30; H, 4.98; N, 5.32%. Found: C, 58.97; H, 5.05; N, 5.29%.

The more polar isomer was 1-(2-methyl-1-phenylsulfonylpyrrol-4-yl)ethanone. It was isolated as a crystalline solid; m.p. 97°–98° C.; 7.1 g (24%).

¹H-NMR(CDCl₃)ppm(delta): 2.36 (s, 3H), 2.46 (s, 3H), 6.37 (bs, 1H), 7.5–7.9 (m, 6H).

Analysis calculated for $C_{13}H_{13}NO_3S$: C, 59.30; H, 4.98; N, 5.32%. Found: C, 59.39; H, 5.06; N, 5.30%.

B. 1-2-Methyl-1-phenylsulfonylpyrrol-5-yl)ethanone

Acetic anhydride (12.7 g, 11.8 ml, 0.125 mole) and 300 ml of 1,2-dichloroethane were combined in a one-liter, three-neck, round-bottomed flask at room temperature under nitrogen, and to this was added dropwise over 15 minutes 35.5 g (31 ml, 0.25 mole) of boron trifluoride etherate. After stirring at room temperature for 15 minutes, a solution of 24.6 g (0.11 mole) 2-methyl-1-phenylsulfonylpyrrole in 135 ml of 1,2-dichloromethane was added dropwise over 15 minutes. The mixture was stirred at room temperature for 1.5 hours, then poured cautiously into ice-water and extracted with methylene chloride (3×250 ml). The combined extracts were dried (Na₂SO₄), filtered, and evaporated leaving an oil. Chromatography over silica gel using 10:10:1 toluene/hexane/ethyl acetate afforded 23.5 g (81%) of the product as a white crystalline solid; m.p. 67°–69° C.

C. The following acetylpyrrole compounds were also obtained by the above method.

| Acetylpyrrole | % Yield | m.p. °C |
|---|---|---|
| pyrrole(N-SO₂C₆H₅)-COCH₃ | 81 | 97.5–99 |

EXAMPLE 4

A.
1-(2-Methyl-1-phenylsulfonylpyrrol-4-yl)-2-bromoethanone

A solution of 13.3 g (50 mmole) of 1-(2-methyl-1-phenylsulfonyl-pyrrol-4-yl)-1-ethanone in 320 ml of chloroform was stirred at −10° C. and a solution of 2.56 ml (8.0 g, 50 mmole) of bromine in 40 ml of chloroform was added dropwise over six hours. After the addition was completed, the mixture was stirred at −10° C. for 0.5 hours, then allowed to warm to room temperature. The mixture was concentrated, and the residue was chromatographed over silica gel using 1:1:0.1 hexane/toluene/ethyl acetate as eluent to give 10.0 g (59%) of the product as a white solid; m.p. 86°–88° C.

B.
1-(2-Methyl-1-phenylsulfonylpyrrol-3-yl)-2-bromoethanone

By employing 1-(2-methyl-1-phenylsulfonyl-pyrrol-3-yl)-2-bromoethanone as starting material in the above procedure provides the title compound in 61% yield; m.p. 108.5°–110.5° C.

Analysis calculated for $C_{13}H_{12}BrNO_3S$: C, 45.63; H, 3.53; N, 4.09%. Found: C, 45.58; H, 3.54; N, 4.08%.

C. By employing the appropriate acetylpyrrole in the above method the following bromoethanones were obtained in like manner.

| Bromoethanone | % Yield | M.P., °C. | Analysis |
|---|---|---|---|
| CH$_3$—[pyrrole]—COCH$_2$Br, N-SO$_2$C$_6$H$_5$ | 55 | 82.5–83.5 | $C_{13}H_{12}BrNO_3S$: C, 45.63; H, 3.53; N, 4.09%. (C, 45.58; H, 3.50; N, 4.07%.) |
| [pyrrole]—COCH$_2$Br, N-SO$_2$C$_6$H$_5$ | 77 | 78.5–80 | — |

EXAMPLE 5

A.
N-[4-(2-N,N-Dimethylaminocarbonylpyrrol-4-yl)thiazol-2-yl]guanidine acetate A mixture of 24.1 g (0.112 mole) 1-(2-N,N-dimethylaminocarbonylpyrrol-4-yl)-2-chloroethanone, 13.8 g (0.117 mole) amidinothiourea, 600 mg of sodium iodide, and 460 ml of acetone was heated at reflux for seven hours. The precipitated solid was collected from the hot mixture and washed well with acetone. The solid was stirred vigorously in one liter of saturated sodium bicarbonate solution for two hours, collected, washed well with water and allowed to dry. The solid material was dissolved in glacial acetic acid (one liter), then evaporated to dryness. Recrystallization of the solid residue from methanol afforded 32.6 g (86%) of the product as a crystalline solid; m.p. >250° C.

Analysis calculated for $C_{11}H_{14}N_6OS·CH_3CO_2H$: C, 46.14; H, 5.36; N, 24.84; S, 9.47%. Found: C, 45.70; H, 5.26; N, 24.79; S, 9.21%.

B. In like manner the corresponding compounds of the formula below were obtained by the above method from the appropriate 1-pyrrolyl-2-haloethanone intermediate.

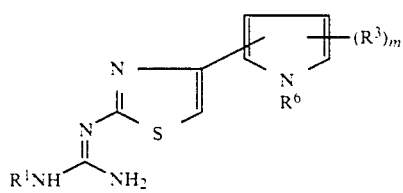

| R$^1$ | [pyrrole ring with (R$^3$)$_m$, N-R$^6$] | % Yield | m.p., °C. | Empirical Formula: Analysis Calculated: (Analysis Found): |
|---|---|---|---|---|
| H | CON(CH$_3$)$_2$, CH$_3$, N-H | 88 | >235 | $C_{12}H_{16}N_6OS·CH_3COOH·0.5H_2O$: C, 46.52; H, 5.86; N, 23.25%. (C, 46.12; H, 5.61; N, 22.82%.) |
| H | NH, C(=O)-N(piperidine) | 85 | >235 | $C_{14}H_{18}N_6OS·HCl·0.5H_2O$: C, 46.21; H, 5.54; N, 23.10%. (C, 46.26; H, 5.30; N, 22.71%.) |
| H | NCH$_3$, CHO | 46 | 250 | $C_{10}H_{11}N_5O_5·CH_3COOH$: C, 46.59; H, 4.89; N, 22.64; S, 10.36%. (C, 46.69; H, 4.85; N, 22.40; S, 10.22%.) |

-continued

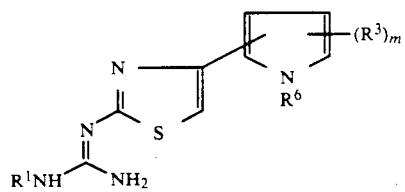

| R¹ | ![pyrrole with R⁶, (R³)ₘ] | % Yield | m.p., °C. | Empirical Formula: Analysis Calculated: (Analysis Found): |
|---|---|---|---|---|
| C₆H₅CH₂ | 2-methyl-pyrrol (N-H) | 57 | 120.5–121.5 | C₁₅H₁₅N₅S.1.5CH₃COOH: C, 55.80; H, 5.46; N, 18.08; S, 8.27%. (C, 55.72; H, 5.45; N, 17.69; S, 8.44%) |
| H | 2-methyl-pyrrol (N-H) | 13 | 231–233 | C₈H₉N₅S.CH₃COOH: C, 44.93; H, 4.90; N, 26.20; S, 12.00%. (C, 45.09; H, 4.98; N, 25.64; S, 11.95%.) |
| CH₃(CH₂)₅ | 2-methyl-pyrrol-4-yl | | | C₁₅H₂₃N₅S: |

EXAMPLE 6

A.
N-[4-(2-N,N-Dimethylaminomethylpyrrol-4-yl)thiazol-2-yl]guanidine acetate A slurry of 2.5 g (6.7 mmole) of N-[4-(2-N,N-dimethylaminocarbonylpyrrol-4-yl)thiazol-2-yl]guanidine acetate in 100 ml dry tetrahydrofuran (THF) was stirred at room temperature under nitrogen, and to this was added 67 ml (67 mmole) 1M borane/THF solution (Aldrich). The reaction mixture was stirred at room temperature for 20 hours. To this was cautiously added 34 ml 6N hydrochloric acid while maintaining the temperature of the reaction mixture at <50° C. with an ice-bath. After the addition was completed, the mixture was heated at 80° C. for 30 minutes, again cooled with an ice-bath and made basic with 10N sodium hydroxide. The aqueous solution was extracted with n-butanol (4×85 ml) and the combined extracts were dried (Na₂SO₄), filtered, and evaporated in vacuo to afford an oil which was purified by chromatography over silica gel using 14:1:1 methylene chloride/methanol/ammonium hydroxide as eluent to give a yellow foam. This was dissolved in glacial acetic acid and concentrated to give an oil which crystallized after trituration with ethyl acetate and scratching with a glass rod. The amount of product isolated was 0.23 g (11%); m.p. 154°–156° C.

Analysis calculated for C₁₁H₁₆N₆S.1.5CH₃CO₂H: C, 47.44; H, 6.26; N, 23.71%. Found: C, 47.57; H, 6.29; N, 23.89%.

B. By employing the appropriate pyrrole carboxamide, provided in Part B of the preceding Example, in the procedure of Part A, above, the corresponding dialkylaminomethylsubstituted pyrrole derivatives of the following formula were similarly obtained. Likewise, formylpyrroles were converted to methylsubstituted pyrroles by the same procedure.

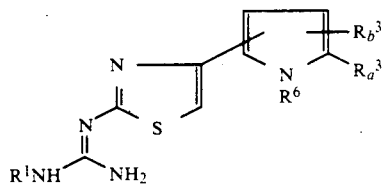

| R¹ | pyrrole with R_a³, R_b³, R⁶ | % Yield | M.P., °C. | Empirical Formula: Analysis Calculated: (Analysis Found): |
|---|---|---|---|---|
| H | CH₂N(CH₃)₂ / CH₃ pyrrole (N-H) | 22 | 166–166.5 | C₁₂H₁₈N₆S.2CH₃COOH.H₂O: C, 46.14; H, 6.77; N, 20.18%. (C, 45.59; H, 6.64; N, 20.06%.) |

-continued

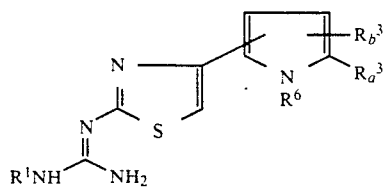

| $R^1$ | ![structure] $R^6$ with $R_b^3$, $R_a^3$ | % Yield | M.P., °C. | Empirical Formula: Analysis Calculated: (Analysis Found): |
|---|---|---|---|---|
| H | ![pyrrole-NH-CH₂N(piperidine), CH₃] | 15 | 175 | $C_{14}H_{20}N_6S \cdot CH_3COOH \cdot 0.5H_2O$: C, 51.45; H, 6.75; N, 22.50%. (C, 51.49; H, 6.60; N, 22.56%.) |
| H | ![pyrrole-NCH₃, CH₃] | 47 | 220–222 | $C_{10}H_{13}N_5S \cdot CH_3COOH$: C, 48.79; H, 5.80; N, 23.71; S, 10.86% (C, 48.49; H, 5.75; N, 23.57; S, 10.90%.) |

EXAMPLE 7

A.

N-[4-(2-Methyl-1-phenylsulfonylpyrrol-4-yl)thiazol-2-yl]guanidine hydrochloride hydrate

A mixture of 10 g (29 mmole) 1-(2-methyl-1-phenylsulfonylpyrrol-4-yl)-2-bromoethanone, 3.4 g (29 mmole) amidinothiourea, and 100 ml acetone was stirred at room temperature for one hour. The resulting precipitate was collected, washed with acetone, and dried in vacuo to give 12.1 g (85%) of the product as its hydrobromide salt. This was converted into its hydrochloride hydrate by stirring in a mixture of 1:2 saturated sodium bicarbonate solution/methanol, concentrating to dryness and triturating the solid residue with ethanol (4x). The ethanol residue was concentrated, the residue dissolved in a minimum of acetone and two equivalents of concentrated hydrochloric acid were added. The resulting precipitate was collected, washed with ether, and dried in vacuo to afford the title compound as a pale yellow solid; m.p..214°–216° C.

Analysis calculated for $C_{15}H_{15}N_5O_2S_2 \cdot HCl \cdot H_2O$: C, 43.32; H, 4.36; N, 16.84; S, 15.42%. Found: C, 43.60; H, 4.26; N, 16.75; S, 15.88%.

B. The compounds of the formula below were similarly obtained from the appropriately substituted pyrrolyl bromoethanone by the above procedure.

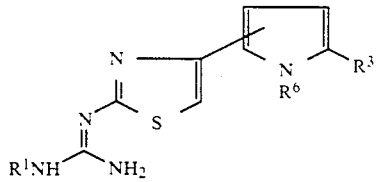

| $R^1$ | ![pyrrole with $R^3$, $R^6$] | % Yield | M.P., °C. | Empirical Formula: Analysis Calculated: (Analysis Found): |
|---|---|---|---|---|
| $C_6H_5CH_2$ | ![pyrrole-NSO₂C₆H₅, CH₃] | 70 | 219–220 | $C_{22}H_{21}N_5O_2S_2 \cdot HBr$: C, 49.93; H, 4.16; N, 13.15; S, 12.04%. (C, 49.38; H, 3.92; N, 13.10; S, 12.27%.) |
| H | ![pyrrole-NSO₂C₆H₅] | 58 | 207.5–209 | $C_{15}H_{15}N_5O_2S \cdot HCl \cdot 0.5H_2O$: C, 44.27; H, 4.21; N, 17.24; S, 15.76%. (C, 44.61; H, 4.12; N, 16.96; S, 15.90%.) |
| $C_6H_5CH_2$ | ![pyrrole-NSO₂C₆H₅] | 73 | 199.5–200.5 | $C_{22}H_{21}N_5O_2S_2 \cdot HBr$: C, 49.63; H, 4.16; N, 13.15%. (C, 49.41; H, 4.07; N, 13.03%.) |

-continued

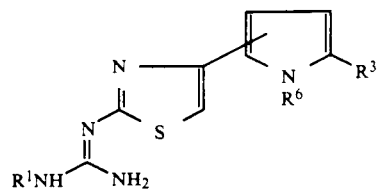

| R¹ | ![R³/R⁶ pyrrole] N-R⁶, R³ | % Yield | M.P., °C. | Empirical Formula: Analysis Calculated: (Analysis Found): |
|---|---|---|---|---|
| H | N(SO₂C₆H₅), CH₃ (both sides) | 64 | 203–204 | $C_{15}H_{15}N_5O_2S_2 \cdot HCl \cdot 0.5H_2O$: C, 44.27; H, 4.21; N, 17.21%. (C, 44.82; H, 4.12; N, 16.91%.) |
| $C_6H_5CH_2$ | N(SO₂C₆H₅), CH₃ | 49 | 125–128 | $C_{22}H_{21}N_5O_2S_2 \cdot HCl \cdot H_2O$: C, 50.61; H, 4.63; N, 13.42%. (C, 50.97; H, 4.55; N, 14.00%.) |
| H | NSO₂C₆H₅ pyrrole | 87 | 246.5–247.5 | $C_{14}H_{13}N_5O_2S_2 \cdot HBr$: |

EXAMPLE 8

A. N-[4-(2-Methylpyrrol-4-yl)thiazol-2-yl]guanidine

A mixture of 12.1 g (25 mmole) of N-[4-(2-methyl-1-phenylsulfonylpyrrol-4-yl)thiazol-2-yl]guanidine hydrobromide, 12.1 g 85% potassium hydroxide and 400 ml methanol was heated at reflux for 18 hours. The mixture was cooled, evaporated to dryness, and the residue triturated with water. The resulting precipitate was collected, washed with water, and dried in vacuo to give 5.3 g (96%) of the product as its free base; m.p. 235°–237° C.

Analysis calculated for $C_9H_{11}N_5S$: C, 48.85; H, 5.01; N, 31.65; S, 14.49%. Found: C, 48.66; H, 5.04; H, 31.37; S, 14.46%.

The acetate salt was obtained by the method of Example 5, Part A.

B. The compounds of the formula below were obtained from the appropriate N-sulfonylpyrrole by the above method.

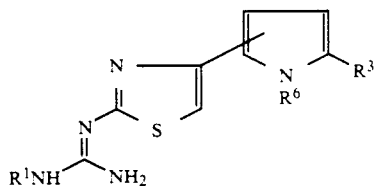

| R¹ | R³/R⁶ pyrrole | % Yield | M.P., °C. | Empirical Formula: Analysis Calculated: (Analysis Found): |
|---|---|---|---|---|
| $C_6H_5CH_2$ | N, CH₃ | 81 | 115.5–118.5 | $C_{16}H_{17}N_5S \cdot CH_3CO_2H \cdot 0.5H_2O$: C, 56.78; H. 5.83; N, 18.41; S, 8.43%. (C, 56.32; H, 5.70; N, 17.85; S, 8.38%.) |
| H | CH₃, NH | 59 | 193–195 | $C_9H_{11}N_5S \cdot CH_3COOH$: C, 46.96; H, 5.37; N, 24.89; S, 11.40%. (C, 47.18; H, 5.55; N, 24.35; S, 11.85%.) |
| $C_6H_5CH_2$ | CH₃, NH | 53 | 102–104 | $C_{16}H_{17}N_5S \cdot 2CH_3COOH \cdot 0.5H_2O$: C, 54.53; H, 5.95; N, 15.90; S, 7.28%. (C, 54.48; H, 5.66; N, 15.50; S, 7.19%.) |

-continued

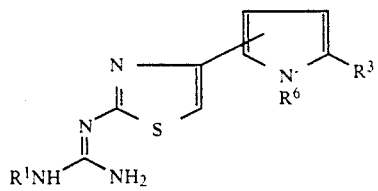

| $R^1$ | $R^3$ $N$ $R^6$ | % Yield | M.P., °C. | Empirical Formula: Analysis Calculated: (Analysis Found): |
|---|---|---|---|---|
| H | (N-H, CH₃ pyrrole) | 25 | 195–198 | $C_9H_{11}N_5S \cdot CH_3COOH$: C, 46.96; H, 5.37; N, 24.89; S, 11.40%. (C, 46.56; H, 5.39; N, 24.06; S, 11.21%.) |
| $C_6H_5CH_2$ | (N-H, CH₃ pyrrole) | 20 | 113–115 | $C_{16}H_{17}N_5S$: M.S. (m/e): Molecular ion: 311.1205 (311.1246) |
| H | (NH pyrrolinyl) | 63 | 246–247.5 | $C_8H_9N_5S \cdot CH_3CO_2H$: C, 44.93; H, 4.90; N, 26.20; S, 12.00%. (C, 44.72; H, 4.91; N, 26.22; S, 11.59%.) |

EXAMPLE 9

A. 1-(1H-Indol-3-yl)-2-chloroethanone

To a stirred solution of 6.00 g (51.2 mmole) indole and 4.2 ml (47.5 mmole) pyridine in 50 ml toluene at 55° C. was added dropwise 5.85 g (51.8 mmole) chloroacetyl chloride. The resulting orange-colored mixture was stirred at 55° C. for 90 minutes and cooled to room temperature. Water (150 ml) and methanol (25 ml) were added and the mixture stirred for another hour. The precipitate was collected, washed with water (50 ml) and dried to give 10.18 g of crude product. This was triturated with chloroform, filtered, the solid washed with chloroform and crystallized from methanol to afford 2.35 g (23%) of product; m.p. 236°–237° C. Reworking the mother liquors gave a second crop which was purified by flash chromatography on silica gel. Two recrystallizations of this product gave an analytically pure product; m.p. 236°–237° C.

Analysis calculated for $C_{10}H_8NOCl$: C, 62.03; H, 4.16; N, 7.23%. Found: C, 62.38; H, 4.23; N, 6.97%.

B. The following compounds were also obtained by reaction of the appropriately substituted indole with chloroacetyl chloride or bromopropionyl bromide by the above method.

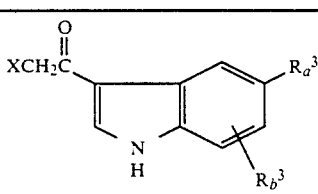

where X is Cl:

| $R_a^3$ | $R_b^3$ | % Yield | M.P., °C. |
|---|---|---|---|
| $CH_3O$ | H | 39 | 267–268 |
| Cl | H | 16 | 269–270 |
| $C_6H_5CH_2O$ | H | 86 | 209–210 |
| H | 2-$CH_3$ | 23 | 206–210 |
| H | 4-$CH_3$ | 17 | 198–199 |
| $CH_3$ | H | 27 | 256–257 |
| H | 6-$CH_3$ | 42 | 243–244 |
| H | 7-$CH_3$ | 36 | 183–184 |
| $NHCOCH_3$ | H | 15 | 248–249 |

EXAMPLE 10

A. 4-(1H-Indol-3-yl)-2-(N-benzyl-N''-guanidino)thiazole Hydrochloride

To a solution of 2.00 g (10.3 mmole) 1-(1H-indol-3-yl)-2-chloroethanone in 80 ml acetone was added 2.15 g (10.3 mmole) benzylguanylthiourea. The mixture was heated at reflux for 17 hours and cooled to room temperature. The precipitated solid was collected by filtration, washed with acetone and dried in vacuo to give 3.12 g (79%) of the title compound; m.p. 266°–267° C.

Analysis calculated for $C_{19}H_{17}N_5S \cdot HCl$: C, 59.44; H, 4.73; N, 18.24%. Found: C, 59.00; H, 4.78; N, 18.12%.

B. Employing the appropriately substituted 3-chloroacetylindole and guanylthiourea in the above procedure afforded compounds of the formula below in like manner.

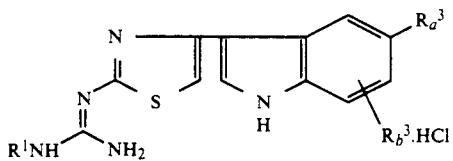

| R¹ | Rₐ³ | R_b³ | % Yield | M.P., °C. | (Footnote No.) |
|---|---|---|---|---|---|
| H | H | H | 80 | 293–295 | |
| C₆H₅CH₂ | CH₃O | H | 71 | 255–256 | (1) |
| H | CH₃O | H | 77 | 259–260 | (2) |
| H | Cl | H | 66 | 305–306 | (3) |
| C₆H₅CH₂ | Cl | H | 49 | 267–268 | (4) |
| H | C₆H₅CH₂O | H | 57 | 243–244 | (5) |
| C₆H₅CH₂ | C₆H₅CH₂O | H | 42 | 200–201 | (6) |
| C₆H₅CH₂ | H | 4-CH₃ | 1 | 125–126 | (7) |
| H | CH₃ | H | 71 | 294–295 | (8) |
| C₆H₅CH₂ | CH₃ | H | 68 | 253–256 | (9) |
| H | H | 6-CH₃ | 68 | 274–275 | (10) |
| C₆H₅CH₂ | H | 6-CH₃ | 73 | 257–258 | (11) |
| H | H | 7-CH₃ | 81 | 288–289 | (12) |
| C₆H₅CH₂ | H | 7-CH₃ | 81 | 284–285 | (13) |
| H | H | 2-CH₃ | 77 | 235–240 | (18) |
| C₆H₅CH₂ | H | 2-CH₃ | 33 | 185 | (19) |
| H | Br | H | 76 | 297–298 | (14) |
| C₆H₅CH₂ | Br | H | 70 | 260–261 | (15) |
| H | F | H | 94 | 286–287 | (20) |
| C₆H₅CH₂ | F | H | 52 | 254–255 | (21) |
| H | CO₂CH₃ | H | 23 | 212–214 | (17) |
| C₆H₅CH₂ | CO₂CH₃ | H | 22 | 255–256 | (16) |
| H | CN | H | 22 | 331–332 | (22) |
| C₆H₅CH₂ | CN | H | 20 | 239–241 | (23) |
| C₆H₅CH₂ | NHCOCH₃ | H | 24 | 166–168 | (24) |

(1) Analysis Calculated for C₂₀H₁₉N₅OS·HCl:
  C, 58.03; H, 4.87; N, 16.92%.
  Found: C, 57.60; H, 4.91; N, 17.19%.
(2) Analysis Calculated for C₁₃H₁₃N₅OS·HCl:
  C, 48.22; H, 4.36; N, 21.63%
  Found: C, 48.42; H, 4.34; N, 21.70%.
(3) Analysis Calculated for C₁₂H₁₀N₅SCl·HCl:
  C, 43.91; H, 3.38; N, 21.34%.
  Found: C, 44.25; H, 3.46; N, 21.50%.
(4) Analysis Calculated for CH₁₉H₁₆N₅SCl·HCl:
  C, 54.55; H, 4.10; N, 16.74%.
  Found: C, 53.56; H, 3.87; N, 16.46%.
(5) Analysis Calculated for C₁₉H₁₇N₅OS·HCl:
  C, 57.07; H, 4.54; N, 17.51%.
  Found: C, 56.94; H, 4.29; N, 17.47%.
(6) Analysis Calculated for C₂₆H₂₄N₅OS·HCl:
  C, 62.58; H, 5.05; N, 14.03%.
  Found: C, 62.43; H, 4.76; N, 14.16%.
(7) High resolution mass spectrum (m/e) for C₂₀H₁₉N₅S:
  Calculated: 361.1357
  Found: 361.1303.
(8) Analysis Calculated for C₁₃H₁₃N₅S·HCl:
  C, 50.72; H, 4.58; N, 22.75%.
  Found: C, 50.86; H, 4.65; N, 22.72%.
(9) Analysis Calculated for C₂₀H₁₉N₅S·HCl·0.5H₂O:
  C, 59.03; H, 5.20; N, 17.21%.
  Found: C, 59.17; H, 4.99; N, 17.28%.
(10) Analysis Calculated for C₁₃H₁₃N₅S·HCl:
  C, 50.72; H, 4.58; N, 22.75%.
  Found: C, 50.73; H, 4.66; N, 22.75%.
(11) Analysis Calculated for C₂₀H₁₉N₅S·HCl·0.5H₂O:
  C, 59.03; H, 5.20; N, 17.21%.
  Found: C, 59.24; H, 4.97; N, 17.40%.
(12) Analysis Calculated for C₁₃H₁₃N₅S·HCl:
  C, 50.72; H, 4.58; N, 22.75%.
  Found: C, 50.37; H, 4.56; N, 22.56%.
(13) Analysis Calculated for C₂₀H₁₉N₅S·HCl·0.5H₂O:
  C, 59.03; H, 5.20; N, 17.21%.
  Found: C, 58.82; H, 4.96; N, 17.37%.
(14) Analysis Calculated for C₁₂H₁₀BrN₅S·HCl:
  C, 38.67; H, 2.98; N, 18.79%.
  Found: C, 38.38; H, 3.03; N, 18.38%.
(15) Analysis Calculated for C₁₉H₁₆BrN₅S·HCl·0.5H₂O:
  C, 48.36; H, 3.84; N, 14.84%.
  Found: C, 47.94; H, 3.66; N, 14.80%.
(16) Analysis Calculated for C₂₁H₁₉N₅SO₂·HCl·H₂O:
  C, 54.60; H, 4.48; N, 15.20%.
  Found: C, 54.84; H, 4.82; N, 15.23%.
(17) Analysis Calculated for C₁₄H₁₃N₅SO₂·HCl·0.25H₂O:
  C, 47.26; H, 4.11; N, 19.68%.
  Found: C, 47.47; H, 3.86; N, 19.42%.
(18) Analysis Calculated for C₁₃H₁₃N₅S·2HCl:
  C, 45.35; H, 4.39; N, 20.34%.
  Found: C, 45.58; H, 4.40; N, 20.00%.
(19) Analysis Calculated for C₂₀H₁₉N₅S·HCl·H₂O:
  C, 57.75; H, 5.33; N, 16.83%.
  Found: C, 57.72; H, 5.07; N, 16.47%.
(20) Analysis Calculated for C₁₂H₁₀FN₅S·HCl:
  C, 46.23; H, 3.56; N, 22.47%.
  Found: C, 45.86; H, 3.54; N, 22.05%.
(21) Analysis Calculated for C₁₉H₁₆FN₅S·HCl·0.75H₂O:
  C, 54.93; H, 4.49; N, 16.86%.
  Found: C, 54.84; H, 4.04; N, 16.73%.
(22) Analysis Calculated for C₁₃H₁₀N₆S·HCl:
  C, 48.98; H, 3.48; N, 26.36%.
  Found: C, 49.17; H, 3.69; N, 26.19%.
(23) Analysis Calculated for C₂₀H₁₆N₆S·HCl·0.5H₂O:
  C, 57.48; H, 4.34; N, 20.11%.
  Found: C, 57.49; H, 4.00; N, 20.05%.
(24) High resolution mass spectrum (m/e) for C₂₁H₂₀N₆OS
  Calculated: 404.1417
  Found: 404.1454

EXAMPLE 11

1-(1H-Indol-2-yl)-2-bromoethanone

A. To a suspension of 21.5 g (133 mmole) indol-2-ylcarboxylic acid, 270 ml acetyl chloride and 270 ml ethyl ether was slowly added 30.4 g (146 mmole) phosphorus pentachloride, the mixture warmed to reflux for one hour after the addition was completed, then allowed to cool to room temperature. The volatiles were removed by evaporation in vacuo and the resulting brown powder recrystallized from heptane to provide 14.9 g (62%) indol-2-ylcarboryl chloride; m.p. 109°–111° C. which was used in the next step.

B. To a two phase mixture of 40% aqueous potassium hydroxide (23.5 g potassium hydroxide in 35 ml water) and 200 ml ethyl ether was added cautiously at 0° C. 12.9 g (88 mmole) N-methyl-N'-nitro-N-nitrosoguanidine. The bright yellow ethereal solution of diazomethane was decanted onto solid, anhydrous potassium hydroxide, dried at 0° C. for two hours, the dried solution decanted into a reaction flask and cooled to 0° C. To this was added 3.01 g (16.7 mmole) finely powdered indol-2-ylcarbonyl chloride in portions. Nitrogen evolution was observed. After stirring at 0° C. for one hour, the mixture was allowed to stand in the refrigerator overnight. The resulting ether solution of 2-diazoacetylindole was cooled to 0° C. and hydrogen bromide gas was bubbled slowly through the solution until it became acidic (pH 1). The resulting solution was carbon treated and the filtrate passed through a short column containing powdered basic alumina. The resulting solution was concentrated to afford 3.31 g (83% over two steps) of the title compound; m.p. 125°–130° C.

C. The following compounds were also obtained by reaction of the appropriately substituted indole-2-yl carboxylic acid in the procedure of Part A, above, and reaction of the resulting acid chloride in the method of Part B.

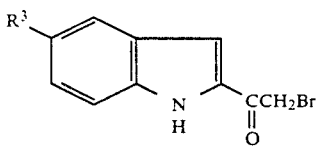

| R³ | % Yield | M.P., °C. |
|---|---|---|
| Cl | 74 | 210–211 |
| F* | 83 | 156–157 |

*2-Substituent is COCH₂Cl.

EXAMPLE 12

A. 4-(1H-Indol-2-yl)-2-guanidinothiazole Hydrobromide

By reaction of 1.31 g (5.48 mmole) 1-(1H-indol-2-yl)-2-bromoethanone with 0.65 g (5.53 mmole) guanylthiourea by the method of Example 10 afforded 1.49 g (80%) of the title salt; m.p. 309°–310° C. (decomp.).

Analysis calculated for $C_{12}H_{11}N_5S \cdot HBr$: C, 42.61; H, 3.58; N, 20.71%. Found: C, 42.97; H, 3.67; N, 20.81%.

B. In the same manner 1.89 g (7.95 mmole) 1-(1H-indol-2-yl)-2-bromoethanone was condensed with 1.66 g (7.95 mmole) benzylguanylthiourea to yield 2.86 g (84%) 4-(1H-indol-2-yl)-2-(N-benzyl-N″-guanidino)-thiazole hydrobromide; m.p. 294°–296° C.

Analysis calculated for $C_{19}H_{17}N_5S \cdot HBr$: C, 53.28; H, 4.24; N, 16.35%. Found: C, 53.09; H, 4.25; N, 16.12%.

C. The following compounds were obtained in like manner.

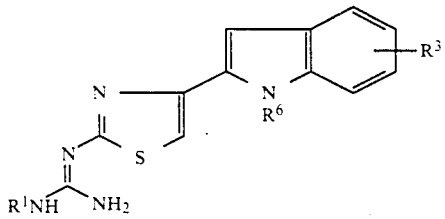

| R¹ | R³ | R⁶ | % Yield | M.P., °C. | Empirical Formula |
|---|---|---|---|---|---|
| C₆H₅CH₂ | 5-Cl | H | 84 | 293–294 | $C_{19}H_{16}ClN_5S \cdot HBr \cdot 0.5 H_2O^{(a)}$ |
| C₆H₅CH₂ | 5-F | H | 81 | 281–282 | $C_{19}H_{16}FN_5S \cdot HCl \cdot 0.25 H_2O^{(b)}$ |
| H | 5-F | H | 89 | 299–300 | $C_{12}H_{10}FN_5S \cdot HCl^{(c)}$ |

Elemental Analysis:
(a)Calculated: C, 48.36; H, 3.84; N, 14.84%.
Found: C, 48.24; H, 3.66; N, 14.94%.
(b)$C_{19}H_{16}FN_5S \cdot HCl \cdot 0.25 H_2O$
Calculated: C, 56.15; H, 4.34; N, 17.23%.
Found: C, 55.81; H, 4.20; N, 17.22%.
(c)$C_{12}H_{10}FN_5S \cdot HCl$
Calculated: C, 46.23; H, 3.56; N, 22.46%.
Found: C, 45.78; H, 3.55; N, 22.25%.

EXAMPLE 13

2-Chloro-1-(2-formylpyrrol-4-yl)propanone

A solution of 37 g (0.39 mole) of pyrrole-2-carboxaldehyde in 425 ml 1,2-dichloroethane was stirred under nitrogen at room temperature. To this was added in portions 312 g (2.34 mole) anhydrous aluminum chloride. After the addition was completed, the mixture was stirred at room temperature for 15 minutes and 113 ml (1.16 mole) 2-chloropropionyl chloride was added dropwise over one hour. The mixture was stirred at room temperature for 20 hours and poured into ice/water. The precipitated solid was removed by filtration and the aqueous layer from the filtrate was separated and washed twice with methylene chloride. The extracts were combined with the organic layer from the filtration, dried, filtered and the solvent evaporated to afford a crude product. This was dissolved in acetone, heated with decolorizing carbon, filtered and the solvent evaporated. After recrystallization from chloroform, the pure title compound, 54.9 g (76%) was obtained; m.p. 96°–99° C.

EXAMPLE 14

2-Guanidino-4-(2-formylpyrrol-4-yl)-5-methylthiazole Hydrochloride

A mixture of 2.5 g (13.5 mmole) 2-chloro-1-(2-formylpyrrol-4-yl)propanone, 1.60 g (13.5 mmole) amidinothiourea, 0.05 g sodium iodide and 75 ml acetone was heated at reflux for 16 hours. A second 0.05 g portion of sodium iodide was added and heating continued for an additional 24 hours. The precipitated solid was collected by filtration, washed with acetone and dried in vacuo to afford 1.20 g (31%) of the title compound; m.p >240° C.

EXAMPLE 15

A. 2-Guanidino-4-(2-methylpyrrol-4-yl)-5-methylthiazole Hydrochloride

A mixture of 1.10 g (3.85 mmole) 2-guanidino-4-(2-formylpyrrol-4-yl)-5-methylthiazole hydrochloride and 50 ml isopropanol was stirred under a nitrogen atmosphere and 0.44 g (11.6 mmole) sodium borohydride was added. The mixture was heated at reflux for six hours, then at room temperature for 14 hours. Methanol (25 ml) was added dropwise, the mixture stirred four hours and concentrated in vacuo. The residue was purified by column chromatography on silica gel, eluting with 9:1 chloroform/methanol (v/v) to give 360 mg of orange foam. The foam was dissolved in acetone, an excess of ethyl ether saturated with hydrogen chloride was added and the precipitated hydrochloride salt collected as 270 mg white solid; m.p. 215°–220° C. (decomp.). Mass spectrum (m/e): 235,0889.

B. By repeating the procedures of Examples 13–15A, but employing the appropriate corresponding starting materials in each case, the following compounds were obtained in like manner.

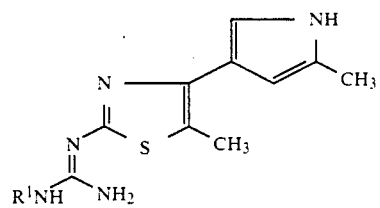

| R¹ | % Yield | M.P., °C. | Empirical Formula |
|---|---|---|---|
| C₆H₅ | 17 | 165–170 (decomp.) | $C_{16}H_{17}N_5S \cdot HCl$ |
| 4-CH₃C₆H₄CH₂ | 20 | 235–240 (decomp.) | $C_{18}H_{21}N_5S \cdot HCl \cdot 0.5 H_2O$ |
| C₆H₅CH₂ | 33 | 205 (decomp.) | $C_{17}H_{19}N_5S \cdot HCl \cdot 0.5 H_2O$ |
| C₆H₅CH₂CH₂ | 29 | 125 | $C_{18}H_{21}N_5S \cdot HCl \cdot H_2O$ |

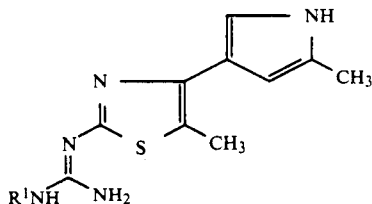

| R[1] | % Yield | M.P., °C. (decomp.) | Empirical Formula: |
| --- | --- | --- | --- |

EXAMPLE 16

2-(N-Benzylguanidino)-4-[(1-phenylsulfonyl-2-methyl-pyrrol-3-yl]-5-methylthiazole monohydrate A. 2-Methyl-1-phenylsulfonyl-3-propionylpyrrole To a slurry of 90.4 g (0.68 mole) anhydrous aluminum chloride in 300 ml 1,2-dichloroethane under nitrogen was added dropwise at room temperature 44.0 ml (0.34 mole) propionic anhydride and the resulting clear amber solution was stirred for 15 minutes after the addition was completed. A solution of 25 g (0.11 mole) 2-methyl-1-phenylsulfonylpyrrole in 100 ml 1,2-dichloroethane was added dropwise and stirring at room temperature continued for 3.5 hours. The reaction was quenched by pouring it into ice. After filtering, the aqueous mixture was extracted with methylene chloride and combined organic layers dried ($Na_2SO_4$) and solvent evaporated in vacuo. The residual oil was triturated with toluene and filtered to afford 14.46 g beige solid; m.p. 105°–110° C. which was used in the next step.

B. 2-Methyl-1-phenylsulfonyl-3-(2-bromopropionyl)pyrrole

Under a nitrogen atmosphere, 14.40 g (0.052 mole) of the above product was dissolved in 300 ml chloroform and the solution cooled to −10° C. A solution of 8.30 g (0.052 mole) bromine in 40 ml chloroform was added dropwise over 6.5 hours. The resulting mixture was warmed to room temperature, washed with saturated sodium bicarbonate solution, the organic layer separated and dried ($Na_2SO_4$). Evaporation of solvent gave a beige solid which was crystallized by suspending it in hexane and slowly adding toluene to effect solution. The solution was heated to reflux, cooled, the crystals collected by filtration and dried; m.p. 99°–103° C.; 14.95 g (81% yield).

C. A mixture of 4.00 g (11.23 mmole) of the product of Part B, above, 2.80 g (13.48 mmole) N-benzylguanylthiourea and 100 ml acetone was heated to reflux for 75 minutes and 0.10 g sodium iodide catalyst added. Heating at reflux was continued for 1.5 hours, the mixture cooled to room temperature and stirred overnight. Heating at reflux was resumed for three hours, the mixture cooled to room temperature and filtered. The filtrate was concentrated in vacuo, the residual foam chromatographed on a silica gel column, eluting with 9:1 chloroform/methanol to yield 4.60 g (75%) of the desired product as a foamed solid; m.p. 110°–115° C. (softens at 60° C.). The structure was verified by its $^1$H-NMR spectrum.

Analysis calculated for $C_{23}H_{23}N_5S_2O_2 \cdot H_2O$: C, 57.12; H, 5.21; N, 14.48%. Found: C, 56.71; H, 4.69; N, 14.20%.

By repeating the above procedure but with N,N-dimethylformamide as solvent in place of acetone and heating at 100° to 120° C. for one hour gives substantially similar results.

D. Hydrolysis of the product obtained in Part C, above, by refluxing in potassium hydroxide in methanol by the method of Example 8, Part A, affords 2-N-benzylguanidino-4-(2-methylpyrrol-3-yl)-5-methylthiazole in like manner.

E. By employing butyryl chloride in place of propionic anhydride in the procedure of Part A, above, affords 2-methyl-1-phenylsulfonyl-3-butyrylpyrrole. When this is reacted in turn by the procedures of Parts B, C and D, above, 2-N-benzylguanidino-5-ethyl-4-(2-methylpyrrol-3-yl)thiazole is obtained.

EXAMPLE 17

A. 1-(5-fluoro-1H-indol-3-yl)-2-chloroethanone

To a stirred solution of 5.00 g (37.0 mmoles) 5-fluoroindole in 65 ml dry ether at 0° C. was added 11.7 ml of 3.18M (37.2 mmoles) methylmagnesium bromide in ether. After stirring at 0° C. for 1 hour, 4.21 g (37.3 mmoles) chloroacetyl chloride was rapidly added. The reaction was stirred at 0° C. for 30 minutes and then 75 ml of 10% aqueous ammonium chloride was added. The mixture was stirred at room temperature for 15 minutes. The mixture was filtered and the solid that was collected was washed with 30 ml of ether and dried to give 2.24 g of a yellow solid. An additional 0.18 g of solid precipitated out of the organic filtrates after 3 days. Both solids consisted of a mixture of mono and diacylated products. These solids were combined and dissolved in 350 ml of methanol. To this solution was added a solution of 1.10 g (8 mmoles) potassium carbonate in 15 ml water. The resulting solution was stirred at room temperature for 16 hours. 500 ml of water was added to the reaction mixture and the mixture was filtered. Washing with 100 ml of water followed by drying gave 1.45 g (19% yield) of 1-(5-fluoro-1H-indolyl)-2-chloroethanone, m.p. 236°–237° C.

B. The following compounds were also obtained by the above procedure, but with the appropriately substituted indole and α-chloroalkanoyl chloride or α-bromoalkanoyl bromide.

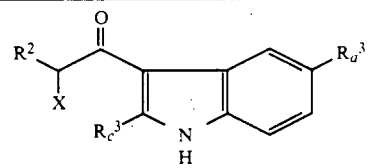

| $R^2$ | $R_a^3$ | $R_c^3$ | % Yield | M.P., °C. |
| --- | --- | --- | --- | --- |
| Where X is Cl: | | | | |
| H | Cl | H | 17 | 269–270 |
| H | $CO_2CH_3$ | H | 40 | 266–267 |
| H | CN | H | 55 | 308–309 |
| H | Br | H | 48 | 276 |
| Where X is Br: | | | | |
| $CH_3$ | Cl | H | 37 | 223–224 |
| $CH_3$ | H | $CH_3$ | 25 | 132–135 |
| $CH_3$ | H | H | 11 | 191–192 |

EXAMPLE 18

5-Chloro-3-(2-bromopropionyl)indole

A. 5-Chloro-3-propionylindole

Friedel-Crafts reaction of propionic anhydride with 5-chloroindole in the presence of molar excess of anhydrous aluminum chloride in chloroform by the method of Example 16, Part A, affords the desired ketone in like manner.

B. Reaction of the compound of Part A, above, with an equimolar amount of bromine in chloroform by the method of Example 16, Part B, affords the title 2-bromoketone; m.p. 223°–224° C.

C. In like manner reaction of the appropriate substituted indole starting compound with propionic, n-butyric or n-pentanoic anhydride, or the corresponding acid chlorides in the procedure of Part A, above, followed by bromination of the resulting ketone by the method of Part B affords the corresponding bromoketones of the formula below.

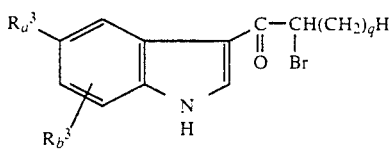

wherein $R_a^3$ and $R_b^3$ are as defined in Example 9 and q is 1, 2, or 3.

EXAMPLE 19

A. 5-Methyl-4-(5-chloro-1H-indol-3-yl)-2-(N″-guanidino)-thiazole, carbon tetrachloride solvate

Equimolar amounts of 5-chloro-3-(2-bromopropionyl)indole and amidinothiourea were reacted in acetone at reflux by the method of Example 10 to afford the title compound; m.p. 160°–170° C. after recrystallization from carbon tetrachloride, yield 42%.

Analysis calculated for $C_{13}H_{12}ClN_5S.O.4CCl_4$: C, 43.81; H, 3.29; N, 19.07%. Found: C, 43.75; H, 3.30; N, 18.99%.

B. By starting with N-benzylguanylthiourea in place of amidinothiourea in the above reaction afforded 5-methyl-4-(5-chloro-1H-indol-3-yl)-2-(N-benzyl-N″-guanidino)thiazole as a carbon tetrachloride solvate; m.p. 166°–167° C. after recrystallization from carbon tetrachloride, yield 62%.

Analysis calculated for $C_{20}H_{18}ClN_5S.O.2CCl_4$: C, 56.68; H, 4.24; N, 16.36%. Found: C, 56.33; H, 4.20; N, 16.22%.

C. In like manner the compounds of the formula below are obtained from the appropriate starting compounds by the above procedures.

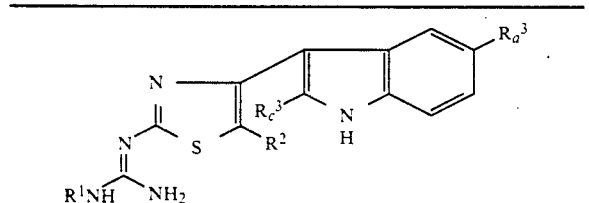

| $R^1$ | $R^2$ | $R_a^3$ | $R_c^3$ | M.P., °C. |
|---|---|---|---|---|
| H | $CH_3$ | H | H | 215–217[a] |
| $C_6H_5CH_2$ | $CH_3$ | H | H | 207–208[b] |
| H | $CH_3$ | H | $CH_3$ | 193–195[c] (HCl salt) |
| $C_6H_5CH_2$ | $CH_3$ | H | $CH_3$ | 185–190[d] (HCl salt) |
| H | $CH_3$ | F | H | — |
| $CH_3(CH_2)_4$ | $CH_2CH_2CH_3$ | $N(CH_3)_2$ | H | — |

[a] 26% yield.
Analysis calculated for $C_{13}H_{13}N_5S.0.4H_2O$: C, 56.06; H, 4.99; N, 25.14%.
Found: C, 56.15; H, 4.75; N, 24.84%.
[b] 49% yield.
Analysis calculated for $C_{20}H_{19}N_5S.0.25H_2O$: C, 65.64; H, 5.37; N, 19.14%.
Found: C, 65.84; H, 5.32; N, 19.12%.
[c] 28% yield.
Analysis calculated for $C_{14}H_{15}N_5S.HCl.0.5H_2O$: C, 50.82; H, 5.18; N, 21.16%.
Found: C, 50.77; H, 5.09; N, 20.99%.
[d] Yellow solid.
Analysis calculated for $C_{21}H_{21}N_5S.HCl.1.5H_2O$: C, 57.45; H, 5.74; N, 15.95%.
Found: C, 57.68; H, 5.38; N, 16.62%.

EXAMPLE 20

2-Guanidino-4-(2-methyl-1H-indol-5-yl)thiazole Hydrochloride

A. By reaction of 2-methylindole with chloroacetyl chloride and anhydrous aluminum chloride by the procedure of Example 16, Part A, affords 1-(2-methylindole-5yl)-2-bromoethanone.

B. The 1-(2-methylindole-5-yl)-2-bromoethanone is reacted with guanylthiourea by the method of Example 12 to afford the title compound as a hemihydrate; m.p. 240° C. (decomp.).

EXAMPLE 21

By employing the methods of Examples 1–8, 15 and 16, pyrrolothiazoles of the formula (II) are obtained in like manner from the appropriate starting compounds of formula (X) and (XIII).

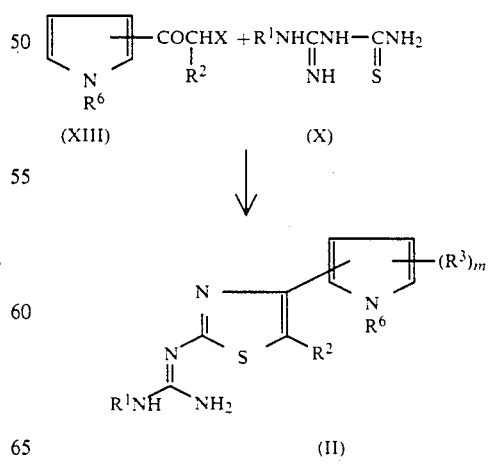

where m, $R^1$, $R^2$, $R^3$, $R^6$ and X are as previously defined.

EXAMPLE 22

By employing the appropriate starting compounds of formula (X) and (XIV) in each case, the compounds of formula (III) are also obtained by the methods of Examples 9–12 and 18–20.

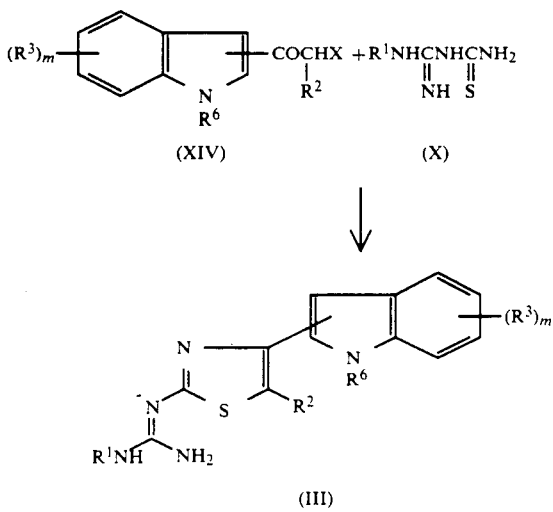

where m, $R^1$, $R^2$, $R^3$, $R^6$ and X are as previously defined.

PREPARATION A

The preparation of requisite 2-arylethylamines of the general formula $(R^4)_pAr^1CH_2CH_2NH_2$, where p, $R^4$ and $Ar^1$ are as previously defined, is exemplified below.

2-(3-Trifluoromethylphenyl)ethylamine (i) 2-(3-trifluoromethylphenyl)acetonitrile A mixture of 12.0 g (61.5 mmole) m-trifluoromethylbenzyl chloride, 9.56 g (195 mmole) sodium cyanide and 60 ml dimethylsulfoxide was heated at 50° to 80° C. for four hours and poured into water. The aqueous mixture was extracted with methylene chloride, the extracts dried over sodium sulfate and the solvent evaporated in vacuo to give 12.2 g of yellow oil which was used in the next step.

$^1$H-NMR(CDCl$_3$)ppm(delta): 3.80 (s, 2H), 7.60 (s, 4H).

(ii) A mixture of 7.20 g (38.9 mmole) 2-(3-trifluoromethylphenyl)acetonitrile, 0.75 g Raney Nickel, 30 ml ethanol and 4.0 ml concentrated ammonium hydroxide was flushed with nitrogen, then hydrogenated at 3.5 kg/cm$^2$ for 18 hours. The catalyst was removed by filtration under nitrogen and the filtrate evaporated in vacuo to afford 6.86 g (93%) of the title amine as a red oil. $^1$H-NMR(CDCl$_3$)ppm(delta): 0.65–1.40 (bs, 2H), 2.65–3.40 (m, 4H), 7.30–7.60 (m, 4H).

PREPARATION B

A general method for preparation of 3-arylpropylamines of the formula $(R^4)_pAr^1(CH_2)_3NH_2$, where p, $R^4$ and $Ar^1$ are as previously defined, below.

3-(4-n-Propylphenyl)propylamine (i) Ethyl 2-cyano-3-(4-n-propylphenyl)acrylate

A mixture of 20.0 g (90 mmole) 4-n-propylbenzaldehyde diethylacetal, 20.4 g (180 mmole) ethyl cyanoacetate, 7.2 g (93.4 mmole) ammonium acetate and 60 ml toluene are heated at reflux for six hours, cooled and poured into water. The resulting mixture was extracted with ethyl ether, dried (MgSO$_4$) and the volatiles evaporated in vacuo to afford 23.0 g crude yellow oil which was purified by chromatography on a silica gel column, eluting with 2:1 methylene chloride/hexane to give 20.58 g (94%) of the desired product.

$^1$H-NMR(CDCl$_3$)ppm(delta): 0.85–1.95 (m, 8H), 2.45–2.70 (t, 2H), 4.15–4.60 (q, 2H), 7.15–805 (q, 4H), 8.25 (s, 1H).

(ii) 3-(4-n-Propylphenyl)propionitrile

A mixture of 20.50 g (84.3 mmole) of the product of Part (i), 8.75 g magnesium turnings and 200 ml methanol was stirred under a nitrogen atmosphere for six hours with periodic cooling to maintain a temperature of about 30° C. The mixture was acidified with hydrochloric acid, extracted with ethyl ether, the extracts washed with sodium bicarbonate solution, water, brine and dried over MgSO$_4$. Evaporation of solvent gave 23.8 g of crude product which was purified by column chromatography on silica gel, eluting with methylene chloride to provide 11.55 g (59%) of purified methyl 2-cyano-3-(4-n-propylphenyl)propionate. This was combined with 4.17 g sodium chloride, 175 ml dimethylsulfoxide and 5 ml water under nitrogen and the mixture heated at 150° C. for five hours. The reaction mixture was cooled, poured into 700 ml water and extracted with 2×500 ml ethyl acetate. The combined extracts were washed with brine (300 ml), dried over anhydrous sodium sulfate and concentrated in vacuo to give 12.5 g of the desired nitrile which was purified by distillation, b.p. 124°–128° C. (1.0 mm).

$^1$H-NMR(CDCl$_3$)ppm(delta): 0.75–1.15 (t, 3H), 1.30–2.00 (m, 2H), 2.40–3.10 (m, 6H), 7.15 (s, 4H).

(iii) A mixture of 14.13 g (81.6 mmole) of the above nitrile (distilled), 1.5 g Raney Nickel, 60 ml ethanol and 8 ml concentrated ammonium hydroxide was hydrogenated at 3.5 kg/cm$^2$ for 18 hours. The mixture was flushed with nitrogen, the catalyst was removed by filtration and the filtrate concentrated in vacuo to give 12.3 g (84.8%) of clear oil. The oil was distilled to provide 8.60 g (59%) of pure amine as a colorless oil.

$^1$H-NMR(CDCl$_3$)ppm(delta): 0.75–1.05 (t, 3H), 1.05 (s, 3H), 1.15–1.75 (m, 4H), 2.30–2.85 (m, 6H), 6.95–7.10 (m, 4H).

PREPARATION C 4-(4-Chlorophenyl)butylamine

A general method for preparation of 4-arylbutylamines of the formula $(R^4)_pAr^1(CH_2)_4NH_2$, where p, $R^4$ and $Ar^1$ are as previously defined, is illustrated below.

(i) 4-(4-Chlorophenyl)-3-butenoic acid

A mixture of 4-chlorobenzaldehyde (10.0 g, 68.2 mmole), 34.0 g (81.9 mmole) 3-(triphenylphosphonium)propionic acid bromide (prepared by reacting triphenylphosphine and 3-bromopropionic acid in xylene), 12.5 g sodium hydride (50% in mineral oil) and 200 ml dimethylsulfoxide were heated at 120° C. for five hours, cooled and poured into ice water. The mixture was made alkaline with sodium carbonate, extracted with ethyl ether and the extracts discarded. The aqueous phase was acidified, extracted again with ethyl ether, dried (MgSO$_4$) and the ether evaporated in vacuo to afford 6.9 g (51%) of the desired acid.

$^1$H-NMR(CDCl$_3$)ppm(delta): 3.10–3.30 (d, 2H), 6.10–6.35 (m, 2H), 7.20 (s, 4H), 11.55–11.75 (bs, 1H).

(ii) 4-(4-Chlorophenyl)butanoic acid

A mixture of 19.5 g (98.2 mmole) of the unsaturated acid from Part (i), above, 1.95 g palladium-on-carbon catalyst and 200 ml ethyl acetate was hydrogenated at 3.5 kg/cm$^2$ and worked up in the usual manner to give the desired saturated acid in 91% yield.

$^1$H-NMR(CDCl$_3$)ppm(delta): 1.75–2.80 (m, 6H), 6.95–7.40 (q, 4H), 9.15–10.25 (bs, 1H).

(iii) 4-(4-Chlorophenyl)butyric acid amide

A mixture of 8.8 g (44.3 mmole) of the saturated acid from Part (ii) and 45 ml thionyl chloride was heated at reflux for three hours. The mixture was cooled and excess thionyl chloride removed by evaporation in vacuo. The crude acid chloride was dissolved in 20 ml ethyl ether and the solution added dropwise to 67 ml concentrated ammonium hydroxide at 0° C. over 20 minutes. A tan solid formed immediately. The mixture was stirred one hour at 0° C., 80 ml water added and the mixture extracted with 3×100 ml ethyl ether. The combined ether layers were washed with brine, dried (MgSO$_4$) and concentrated in vacuo to give 8.70 g (97%) of amide.

$^1$H-NMR(CDCl$_3$)ppm(delta): 1.60–2.40 (m, 4H), 2.45–2.85 (t, 2H), 5.25–6.10 (bs, 2H), 6.90–7.30 (q, 4H).

(iv) A mixture of 8.70 g (44 mmole) of amide from Part (iii), above, and 71 ml 1.0M boron hydride/tetrahydrofuran in 60 ml tetrahydrofuran was stirred four hours and the reaction quenched with 6N hydrochloric acid (36 ml). The mixture was extracted with ethyl ether, the extracts dried (Na$_2$SO$_4$) and concentrated in vacuo. The residual oil was stirred with isopropyl ether, filtered and the filtrate evaporated in vacuo to give 2.08 g. An additional 2.4 g was obtained by extraction of the liquors with ethyl acetate.

$^1$H-NMR(CDCl$_3$)ppm(delta): 1.15 (s, 2H), 1.30–1.90 (m, 4H), 2.40–2.90 (q, 4H), 6.90–7.35 (q, 4H).

We claim:

1. A compound of the formula

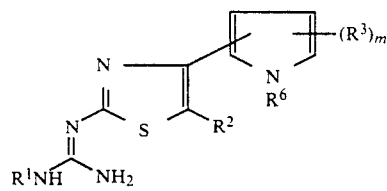

or a pharmaceutically acceptable cationic or acid addition salt thereof
wherein
$R^1$ is H or C$_6$H$_5$CH$_2$;
$R^2$ is H or (C$_1$–C$_4$)alkyl;
m is 1; and
$R^6$ is $R^{10}$SO$_2$ where $R^{10}$ is phenyl and $R^3$ is CH$_3$; or $R^6$ is H and $R^3$ is

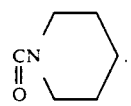

2. A compound according to claim 1 of the formula

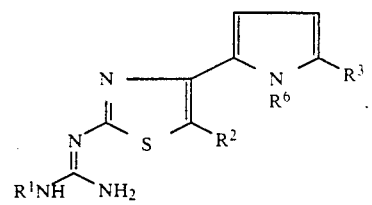

3. A compound according to claim 2 wherein $R^1$ and $R^2$ are each H, $R^6$ is C$_6$H$_5$SO$_2$ and $R^3$ is CH$_3$.

4. A compound according to claim 2 wherein $R^1$ is C$_6$H$_5$CH$_2$, $R^2$ is H, $R^3$ is CH$_3$ and $R^6$ is C$_6$H$_5$SO$_2$.

5. A compound according to claim 2 of the formula

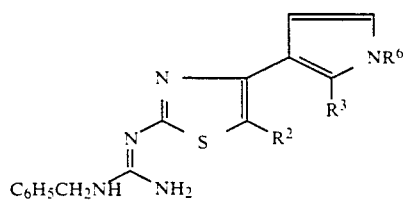

where $R^2$ is H or CH$_3$, $R^6$ is C$_6$H$_5$SO$_2$ and $R^3$ is CH$_3$.

6. A pharmaceutical composition for inhibiting gastric parietal cell H$^+$/K$^+$ ATPase in a mammal which comprises a pharmaceutically acceptable carrier and a gastric parietal cell H$^+$/K$^+$ ATPase inhibiting amount of a compound according to claim 1.

7. A method of treating gastric ulcers by inhibiting parietal cell H$^+$/K$^+$ ATPase in a mammalian subject in need of such treatment which comprises administering to said subject a parietal cell H$^+$/K$^+$ ATPase inhibiting amount of a compound according to claim 1.

8. A compound of the formula

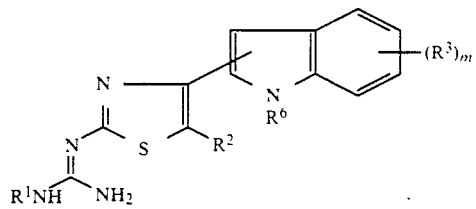

or a pharmaceutically acceptable cationic or acid addition salt thereof, wherein $R^1$ is H, a straight chain or branched chain (C$_1$–C$_{10}$)alkyl, (R$^4$)$_p$C$_6$H$_3$ or (R$^4$)$_p$Ar$^1$(CH$_2$)$_n$ where p is zero, 1 or 2; n is an integer from 1 to 4, the R$^4$ groups are the same or different and are H, F, Cl, Br, I, CH$_3$, CH$_3$O, NO$_2$, OH, CN, COOR$^5$ or OCOR$^5$ and R$^5$ is (C$_1$–C$_3$)alkyl;

Ar$^1$ is the residue of a phenyl, naphthyl, furyl, thienyl, pyridyl, pyrimidinyl, thiazolyl or imidazolyl group, R$^2$ is H or (C$_1$–C$_4$)alkyl;

m is 1, 2 or 3;

R$^6$ is H, (C$_1$–C$_4$)alkyl or R$^{10}$SO$_2$ and R$^{10}$ is (C$_1$–C$_4$)alkyl-, phenyl, tolyl, benzyl or phenylethyl; and at least one R$^3$ is H or (C$_1$–C$_4$)alkyl and each of the remaining R$^3$ is H, (C$_1$–C$_4$)alkyl, (C$_1$–C$_4$)alkoxy, (R$^4$)$_2$C$_6$H$_3$, (R$^4$)$_2$C$_6$H$_3$(CH$_2$)$_n$, (R$^4$)$_2$C$_6$H$_3$(CH$_2$)$_n$O, COOR$^7$, COR$^8$, NHCOR$^8$, NHCH$_2$R$^8$, NR$^8$R$^9$, (CH$_2$)$_n$NR$^8$R$^9$, (CH$_2$)$_{n-1}$CONR$^8$R$^9$, OH, CN, CF₃, F, Cl or Br, wherein n and R⁴ are as previously defined;

R⁷ is H, (C₁-C₄) alkyl or benzyl;

R⁸ and R⁹ taken separately are each H, (C₁-C₁₀)alkyl, phenyl or benzyl, or when taken together with the nitrogen atom to which they are attached, form a 5-membered or 6-membered ring, optionally containing an atom of O or S or the group NR¹¹ as a ring member and R¹¹ is H, methyl or ethyl.

9. A compound according to claim 8 wherein R¹ is H, (R⁴)₂C₆H₃CH₂, (C₄-C₈)alkyl, furylmethyl or thienylmethyl and R³ is H, F, Cl, Br, OH, (C₁-C₄)alkoxy, (C₁-C₄)alkyl, R⁴C₆H₄, NHCOR⁸, (CH₂)ₙNR⁸R⁹, R⁴C₆H₄CH₂O, CN or COOR⁷.

10. A compound of the formula

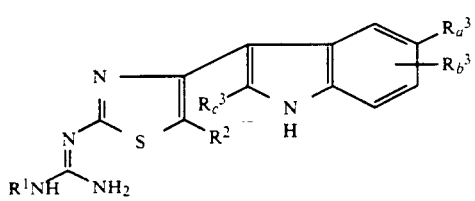

or a pharmaceutically acceptable cationic or acid addition salt thereof
wherein R¹ is H or C₆H₅CH₂; R² is H or CH₃; R_a³ and R_b³ are each H, F, Cl, Br, CH₃, CH₃O, CN, COOCH₃, NHCOCH₃ or C₆H₅CH₂O; and R_c³ is H or (C₁-C₄)alkyl.

11. A compound according to claim 10 wherein R², R_b³ and R_c³ are each H.

12. The compound according to claim 11 wherein R¹ is C₆H₅CH₂ and R_a³ is H.

13. The compound according to claim 11 wherein R¹ is C₆H₅CH₂ and R_a³ is CH₃O.

14. A compound according to claim 11 wherein R¹ is H or C₆H₅CH₂ and R_a³ is Cl, Br, CH₃ or C₆H₅CH₂O.

15. A compound according to claim 11 wherein R¹ is H or C₆H₅CH₂, R², R_a³ and R_c³ are each H and R_b³ is CH₃ attached to the 6-position or the 7-position of the indole substituent.

16. A compound according to claim 10 wherein R¹ is H, or C₆H₅CH₂, R² is CH₃, R_b³ and R_c³ are each H and R_a³ is H or Cl.

17. A compound according to claim 10 wherein R¹ is H or C₆H₅CH₂, R² is H, R_a³ and R_b³ are each H and R_c³ is CH₃.

18. A compound according to claim 10 wherein R¹ is H or C₆H₅CH₂, R² is CH₃, R_a³ is H or CH₃, R_b³ is H and R_c³ is CH₃.

19. The compound according to claim 18 wherein R¹ is H and R_a³ is H.

20. The compound according to claim 18 wherein R¹ is C₆H₅CH₂ and R_a³ is H.

21. A compound according to claim 9 of the formula

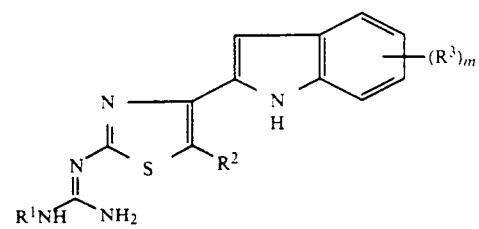

22. A pharmaceutical composition for inhibiting gastric parietal cell H⁺/K⁺ ATPase in a mammal which comprises a pharmaceutically acceptable carrier and a gastric parietal cell H⁺/K⁺ ATPase inhibiting amount of a compound according to claim 8.

23. A method of treating gastic ulcers by inhibiting parietal cell H⁺/K⁺ ATPase in a mammalian subject in need of such treatment which comprises administering to said subject a parietal cell H⁺/K⁺ ATPase inhibiting amount of a compound according to claim 8.

24. An antiinflammatory composition which comprises:
(a) an antiinflammatory effective amount of piroxicam or a pharmaceutically acceptable salt thereof; and
(b) a gastric parietal cell H⁺/K⁺ ATPase inhibiting effective amount of a compound of the formula

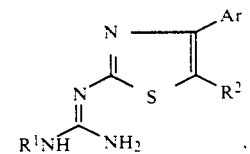

a pharmaceutically acceptable cationic or acid addition salt thereof, wherein
R¹ is H, a straight or branched chain (C₁-C₁₀)alkyl, (R⁴)ₚC₆H₃ or (R⁴)ₚAr¹(CH₂)ₙ where p is zero, 1 or 2; n is an integer from 1 to 4, the R⁴ groups are the same or different and are H, F, Cl, Br, I, CH₃, CH₃O, NO₂, OH, CN, COOR⁵ or OCOR⁵ and R⁵ is (C₁-C₃)alkyl;
Ar¹ is the residue of a phenyl, naphthyl, furyl, thienyl, pyridyl, pyrimidinyl, thiazolyl or imidazolyl group; R² is H or (C₁-C₄)alkyl,
Ar is

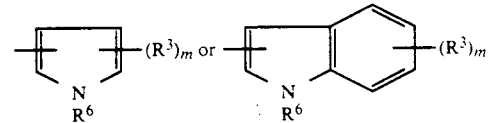

where m is 1, 2 or 3;
R⁶ is H, (C₁-C₄)alkyl or R¹⁰SO₂ and R¹⁰ is (C₁-C₄)alkyl, phenyl, tolyl, benzyl or phenylethyl; and
R³ is a substituent attached to any carbon atom in the Ar group other than one at a ring junction, at least one R³ is H or (C₁-C₄) alkyl and each of the remaining R³ is H, (C₁-C₄)alkyl, (C₁-C₄)alkoxy, (R⁴)₂C₆H₃, (R⁴)₂C₆H₃(CH₂)ₙ, (R⁴)₂C₆H₃(CH₂)ₙO, COOR⁷, COR⁸, NHCOR⁸, NHCH₂R⁸, NR⁸R⁹, (CH₂)ₙNR⁸R⁹, (CH₂)ₙ₋₁CONR⁸R⁹, OH, CN, CF₃, F, Cl or Br wherein n and R⁴ are as previously defined;

$R^7$ is H, $(C_1-C_4)$alkyl or benzyl;

$R^8$ and $R^9$ taken separately are each H, $(C_1-C_{10})$alkyl, phenyl or benzyl, or taken together with the nitrogen atom to which they are attached, form a 5-membered or 6-membered ring, optionally containing an atom of O or S or $NR^{11}$ as a ring member; and $R^{11}$ is H, methyl or ethyl;

with the proviso that when Ar is

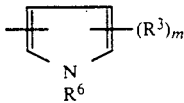

and each $R^3$ is H, at least one of $R^1$, $R^2$ or $R^6$ is other than H.

25. A method of treating inflammation in a mammal which comprises administration to a mammal in need of such treatment:
   (a) an antiinflammatory effective amount of piroxicam or a pharmaceutically acceptable salt thereof; and
   (b) a gastric parietal cell $H^+/K^+$ ATPase inhibiting effective amount of a compound of the formula

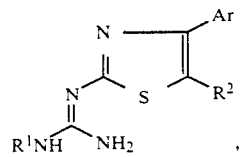

a pharmaceutically acceptable cationic or acid addition salt thereof, wherein $R^1$ is H, a straight or branched chain $(C_1-C_{10})$alkyl, $(R^4)_pC_6H_3$ or $(R^4)_pAr^1(CH_2)_n$ where p is zero, 1 or 2; n is an integer from 1 to 4, the $R^4$ groups are the same or different and are H, F, Cl, Br, I, $CH_3$, $CH_3O$, $NO_2$, OH, CN, $COOR^5$ or $OCOR^5$ and $R^5$ is $(C_1-C_3)$alkyl;

$Ar^1$ is the residue of a phenyl, naphthyl, furyl, thienyl, pyridyl, pyrimidinyl, thiazolyl or imidazolyl group; $R^2$ is H or $(C_1-C_4)$alkyl, Ar is

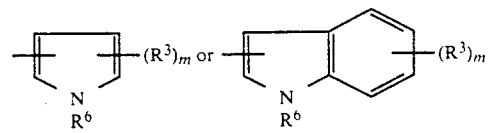

where m is 1, 2 or 3;

$R^6$ is H, $(C_1-C_4)$alkyl or $R^{10}SO_2$ and $R^{10}$ is $(C_1-C_4)$alkyl, phenyl, tolyl, benzyl or phenylethyl; and $R^3$ is a substituent attached to any carbon atom in the Ar group other than one at a ring junction, at least one $R^3$ is H or $(C_1-C_4)$alkyl and each of the remaining $R^3$ is H, $(C_1-C_4)$alkyl, $(C_1-C_4)$alkoxy, $(R^4)_2C_6H_3$, $(R^4)_2C_6H_3(CH_2)_n$, $(R^4)_2C_6H_3(CH_2)_nO$, $COOR^7$, $COR^8$, $NHCOR^8$, $NHCH_2R^8$, $NR^8R^9$, $(CH_2)_nNR^8R^9$, $(CH_2)_{n-1}CONR^8R^9$, OH, CN, $CF_3$, F, Cl or Br wherein n and $R^4$ are as previously defined;

$R^7$ is H, $(C_1-C_4)$alkyl or benzyl;

$R^8$ and $R^9$ taken separately are each H, $(C_1-C_{10})$alkyl, phenyl or benzyl, or taken together with the nitrogen atom to which they are attached, form a 5-membered or 6-membered ring, optionally containing an atom or O or S or $NR^{11}$ as a ring member; and $R^{11}$ is H, methyl or ethyl;

with the proviso that when Ar is

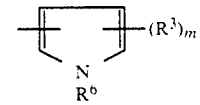

and each $R^3$ is H, at least one of $R^1$, $R^2$ or $R^6$ is other than H.

* * * * *